(12) United States Patent
Zemlan

(10) Patent No.: US 6,589,746 B1
(45) Date of Patent: Jul. 8, 2003

(54) METHOD OF DETECTING AXONALLY-DERIVED PROTEIN TAU IN PATIENTS WITH TRAUMATIC CNS INJURY

(75) Inventor: Frank P. Zemlan, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 0 days.

(21) Appl. No.: 09/694,627

(22) Filed: Oct. 23, 2000

Related U.S. Application Data
(60) Provisional application No. 60/160,690, filed on Oct. 21, 1999.

(51) Int. Cl.$^7$ ....................... G01N 33/53; G01N 33/533; G01N 33/543; G01N 33/567; A61K 39/395

(52) U.S. Cl. ....................... 435/7.1; 435/7.92; 435/7.94; 436/503; 424/130.1; 530/300

(58) Field of Search ........................ 435/35, 69.1, 325, 435/7.1, 7.92; 530/300; 424/130.1, 184.1; 436/503

(56) References Cited

U.S. PATENT DOCUMENTS

| | | | |
|---|---|---|---|
| 5,492,812 A | 2/1996 | Vooheis | 435/7.1 |
| 5,601,984 A | 2/1997 | Kohne | 435/6 |
| 5,733,734 A | 3/1998 | Trojanowski et al. | 435/7.1 |
| 5,861,257 A | 1/1999 | Vandermeeren et al. | 435/7.1 |

OTHER PUBLICATIONS

Pardridge, William M., Receptor–Mediated Peptide Transport through the Blood–Brain Barrier, Endocrin. Rev. 7: 314–330 (1986).
Adams J.H., Doyle D., Ford I., Gennarelli T.A., Graham D.I., and McLellan D.R. (1989) Diffuse axonal injury in head injury: definition, diagnosis and grading. Histopathology 15, 49–59.
Anderton B.H., Breinberg D., Downes M.J., Green P.J., Tomlinson B.E., Ulrich J., Wood J.N., and Kahn J. (1982) Monoclonal antibodies show that neurofibrillary tangles and neurofilaments share antigenic determinants. Nature 298, 84–86.
Binder L.I., Frankfurter A., and Rebhun L.I. (1985) The distribution of tau in the mammalian central nervous system. J. Cell Biol. 101, 1371–1378.
Bobrow M.N., Harris T.D., Shaughnessy K.J. and Litt G.J. (1989) Catalyzed reporter deposition, a novel method of signal amplification. J. Immunol. Meth. 125, 279–285.
Boorsma D.M. and Kalsbeek G.L. (1975) A comparative study of horseradish peroxidase conjugates prepared with a one–step and a two–step process, J. Histochem. Cytochem. 23, 200–207.
Caputo C.B., Wischik C., Novak M., Scott C.W., Brunner W.F., De Garcini E.M., Lo M.M.S., Norris T.E. and Salama A.I. (1992) Immunological characterization of the region of tau protein that is bound to Alzheimer paired helical filaments. Neurobiol. Aging 13, 267–274.
Carmel G., Mager E.M., Binder L.I. and Kuret J. (1996) The structural basis of monoclonal antibody Alz50's selectivity for Alzheimer's disease pathology. J. Biol. Chem. 271, 32789–32795.
Cleveland D.W., Hwo S.Y. and Kirschner M.W. (1977) Purification of tau, a microtubule–associated protein that induces the assembly of microtubules from purified tubulin. J. Mol. Biol. 116, 207–225.
Couchie D. and Nunez J. (1985) Immunological characterization of microtubule–associated proteins specific for the immature brain. FEBS Lett. 188, 331–335.
Goedert M., Spillantini M.G., Jakes R., Rutherford D. and Crowther R.A. (1989) Multiple isoforms of human microtubule–associated protein tau: sequence and localization in neurofibrillary tangles and Alzheimer's disease. Neuron 3, 519–526.
Gotow T. and Tanaka J. (1994) Phosphorylation of neurofilament H subunit as related to arrangement of neurofilaments. J. Neurosci. Res. 37, 691–713.
Greenberg S.G., Davies P., Schein J.D. and Binder L.I. (1992) Hydrofluoric acid–treated PHFτ proteins display the same biochemical properties as normal τ. J. Biol. Chem. 267: 564–569.
Hayes R.L., Yang K., Whitson J.S. and Posmantur R. (1995) Cytoskeletal deragements following central nervous system injury: modulation by neurotropic gene transfection. J. Neurotrauma 12, 933–941.
Julien J.P., Grosveld F., Yazdanbaksh K. et al.: The structure of the human neurofilament gene (NF–L): a unique exon–intron organization in the intermediate gene family. Biochim. Biophys. Acta 909, 10–20.
Kohler G. and Milstein C. (1975) Continuous cultures of fused cells secreting antibody of predefined specificity. Nature 256, 495–497.
Kosik K.S. and Finch E.A. (1987) MAP2 and tau segregate into dendritic and axonal domains after the elaboration of morphologically distinct neurties. J. Neurosci. 7, 3142–3153.

(List continued on next page.)

Primary Examiner—Elizabeth Kemmerer
Assistant Examiner—Sandra Wegert
(74) Attorney, Agent, or Firm—Frost Brown Todd LLC

(57) ABSTRACT

Patients having several neurological diseases have been shown to have elevated levels of axonally-derived proteins (i.e. tau and neurofilament proteins) in cerebrospinal fluid (CSF) and in brain tissue. Three monoclonal antibodies (MAbs) recognizing CSF tau proteins were developed. The MAbs were found to label a ladder of 30 kD to 50 kD tau proteins in CSF from patients with disease states producing axonal damage such as head trauma or CNS tumor but not in CSF from controls. High levels of tau protein in CSF were shown to be diagnostic of axonal degeneration in head trauma. An ELISA assay was developed with these MAbs to aid in the diagnosis of patients with axonal damage.

16 Claims, 6 Drawing Sheets

OTHER PUBLICATIONS

Kosik K.S., Orecchio L.D., Bakalis S. and Neve R.L. (1989) Developmentally regulated expression of specific tau sequences. *Neuron* 2, 1389–1397.

Laemmli, U.K. (1970) Cleavage of structural proteins during the assembly of the head of bacteriophage T4, *Nature* 227, 680–685.

Lee G. and Rook S.L. (1992) Expression of tau protein in non–neuronal cells: microtubule binding and stabilization. *J. Cell Sci*. 102, 227–237.

Lees J.F., Shneidman P.S., Skuntz S.F. et al.: The structure and organization of the human heavy neurofilament subunit (NF–H) and the gene encoding it. *EMBO J*. 7, 1947–1955.

Litman P., Barg J., Rindzoonski L. and Ginsburg I. (1993) Subcellular localization of tau mRNA in differentiating neuronal culture: implications for neuronal polarity. *Neuron* 10, 627–638.

Myers M.W., Lazzarini R.A., Lee V.M. et al.: (1987) The human mid–size neurofilament subunit: a repeat protein sequence and the relationship of its gene to the intermediate filament gene family. *EMBO J*. 6, 1617–1626.

Nukina N., Kosik K.S. and Selkoe D.J. (1987) Recognition of Alzheimer's paired helical filaments by monoclonal neurofilament antibodies is due to crossreaction with tau protein. *Proc. Natl. Acad. Sci. USA* 84, 3415–3419.

Otvos L., Feiner L., Lang E., Szendrei G.I., Goedert M. and Lee V.M.Y. (1994) Monoclonal antibody PHF–1 recognizes tau protein phosphorylated at serine residues 396 and 404 *J. Neurosci. Res*. 39, 669–673.

Schiff P.B., Fant J. and Horwitz S.B. (1979) Promotion of microtubule assembly in vitro by taxol. *Nature* 277, 665–667.

Shaw G. (1986) Neurofilaments: abundant but mysterious structures. *Bioessays* 4, 161–166.

Towbin H., Staehelin T., and Gordon J. (1979) Electrophoretic transfer of proteins from polyacrylamide gels to nitrocellulose sheets: Procedure and some applications. *Proc. Natl. Acad. Sci USA* 76, 4350–4354.

Vallee R.B. (1982) A taxol–dependent procedure for the isolation of microtubules and microtubule–associated proteins (MAPs), *J. Cell Biol*. 92, 435–442.

Vincent I., Rosado M. and Davies P. (1996) Mitotic mechanisms in Alzheimer's disease?. *J. Cell Biol*. 132, 413–425.

Wolozin B.L., Pruchnicki A., Dickson D.W., and Davies P. (1986) A novel antigen in the Alzheimer's brain. *Science* 232, 648–650.

Zemlan F.P. and Dean G.E. (1996) Monoclonal antibody PHF–9 recognizes phosphorylated ser404 of tau protein and labels paired helical filaments. *J. Neurosci. Res*. 46, 90–97.

METHOD OF DETECTING AXONALLY-DERIVED PROTEIN TAU IN PATIENTS WITH TRAUMATIC CNS INJURY

This application is based on and claims priority from U.S. provisional application Ser. No. 60/160,690, Method of Detecting Axonal Damage and Associated Disease States, Zemlan, filed Oct. 21, 1999.

FIELD OF THE INVENTION

The present invention is in the field of clinical and diagnostic testing, and relates generally to a method of detecting axonal damage and associated disease states.

BACKGROUND OF THE INVENTION

Axonal degeneration is a primary feature of brain injury in humans (Hayes et al., 1995). The present invention describes several methods of assessing axon degeneration in humans by measuring proteins that are localized in axons. These axonal proteins are released following head injury into the extracellular space and are transported to cerebrospinal fluid (CSF). Methods are disclosed in the present invention for measuring these axonal proteins in the CSF and blood of patients.

Tau protein is a major microtubule associated structural protein localized primarily in axons (Binder et al. 1985; Kosik and Finch 1987). The localization of tau in axons is thought to result from the preferential sequestration of tau mRNA in the proximal portion of axons (Litman et al., 1993) and the selective stabilization of tau in axons (Kanai and Hirakawa 1995). Human tau proteins are encoded by a single gene and at least six alternately spliced isoforms have been identified that demonstrate an apparent molecular weight of 48 kilodalton (kDa) to 68 kDa (Goedert et al. 1989 and FIG. 5). Under normal conditions, little or no tau is released extracellularly. This disclosure teaches that tau is released under clinical conditions associated with axon damage.

Neurofilament proteins, similar to tau, are structural neuronal proteins found in central nervous system axons (Shaw, 1986). Neurofilaments that are the subject of the present invention consist of four separate protein elements: 1) a light neurofilament subunit (neurofilament-L) with an apparent molecular weight of 68 kDa, 2) a medium-sized neurofilament subunit (neurofilament-M) with an apparent molecular weight of 160 kDa, 3) a heavy neurofilament subunit (neurofilament-H) with an apparent molecular weight of 200 kDa, and 4) neurofilament66/α-intemexin (neurofilament66) with an apparent molecular weight of 66 kDa (Lee and Cleveland, 1996). These neurofilaments are each encoded on a separate gene (Julien et al., 1987; Myers et al., 1987; Lees et al., 1988; Chan and Chiu, 1995). Following head injury neurofilaments are depleted from degenerating axons and gain access to the CSF (Hayes et al., 1995).

One clinical condition associated with axonal degeneration is head trauma. Axonal injury, clinically referred to as diffuse axonal injury, accounts for about half of the primary lesions observed in closed head trauma and is one of the most frequent causes of poor clinical outcome. MRI is the procedure of choice for detecting diffuse axonal injury, however, MRI routinely underestimates the true extent of the damage.

As our understanding of the nervous system and its related disorders increases, a wider range of therapeutic and diagnostic agents will become available. Once these agents have been identified, it will be necessary to detect such diagnostic markers in the central nervous system. Unfortunately, the existence of the blood-brain barrier limits the free passage of many types of molecules from the blood to cells of the central nervous system making it necessary for diagnostic tests to be performed on CSF and blood, serum or plasma.

The physiological basis for the blood-brain barrier is the brain capillaries, which are made of endothelial cells (Goldstein, et al., Scientific American, 255: 74–83 (1986); Pardridge, W. M., Endocrin. Rev. 7:314–330 (1986)). These endothelial cells are different from those found in other tissues of the body. In particular, they form tight junctions between themselves. The actual blood-brain barrier is formed by these high-resistance tight intercellular junctions that form a continuous wall against the passive movement of molecules from the blood to the brain. These cells are also different in that they have few pinocytotic vesicles, which in other tissues allow somewhat unselective transport across the capillary wall. In addition, continuous gaps or channels running through the cells, which would allow unrestrained passage, are absent.

One function of the blood-brain barrier is to protect the brain from fluctuations in blood chemistry. However, this isolation of the brain from the bloodstream is not complete. There does exist an exchange of nutrients and waste products. The presence of specific transport systems within the capillary endothelial cells assures that the brain receives, in a controlled manner, all of the compounds required for normal growth and function. The obstacle presented by the blood-brain barrier is that, in the process of protecting the brain, it excludes many potentially useful therapeutic and diagnostic agents.

There are several techniques that either physically break through the blood-brain barrier or circumvent it to deliver therapeutic or diagnostic agents. Among these are intrathecal injections, surgical implants, and osmotic techniques.

Intrathecal injection administers agents directly into the brain ventricles and spinal fluid by puncturing the membranes surrounding the brain. Sustained dosages of agents directly into the spinal fluid can be attained by the use of infusion pumps that are implanted surgically. These spinal fluid delivery techniques are used to treat brain cancers, infections, inflammation and pain, but only penetrate into a minute fraction of the brain due to diffusion gradients and the density of neural tissues.

Clinicians prefer to avoid intrathecal injections because they frequently are ineffective and can be dangerous. Substances injected intrathecally are distributed unevenly, slowly and incompletely in the brain. Since the volume of the spinal fluid is small, increases in intracerebral pressure can occur with repeated injections. Furthermore, improper needle or catheter placement can result in seizure, bleeding, encephalitis and a variety of other severe side effects.

One embodiment of the present invention involves the development and use of an alternative procedure for quantifying axon damage in patients with CNS injury. Another embodiment of the present invention involves a method for quantifying axonal degeneration which is the central feature of neurodegenerative disorders including Alzheimer's disease. Alzheimer's disease is a progressive, degenerative disease that attacks the brain and results in impaired memory, thinking and behavior. Alzheimer's disease is the most common form of dementia, which is the loss of intellectual function so severe it interferes with daily life. Since being first described by Dr. Alois Alzheimer in 1906, it has become the fourth leading cause of death among adults in the United States between the ages of 75 and 84. The clinical mortality and morbidity seen in Alzheimer's patients directly results from neuronal death in the brain. In neurodegenerative disorders including Alzheimer's disease, neuronal death is always accompanied by axonal degeneration.

Patents that discuss tau protein in serum include U.S. Pat. Nos. 5,492,812, 5,861,257, 5,733,734 and 5,601,985.

To determine the existence vel non of disease or trauma states associated with axonal damage in a patient, it is desirable to be able to ascertain whether a patient has such axonal damage and to quantify such damage.

In view of the present disclosure or through practice of the present invention, other advantages or problem solutions may become apparent.

SUMMARY OF THE INVENTION

The present invention includes a method of determining the extent of axonal damage in the human CNS, novel cleaved forms of tau proteins and neurofilament proteins associated with axonal damage, and monoclonal antibodies (MAbs) raised against novel cleaved forms of tau protein useful in such a method.

In general terms, the method of the present invention is a method of determining axonal damage in the human CNS, the method comprising the steps: (a) obtaining a sample of CSF or blood from the human central nervous system of a patient; (b) treating the sample of CSF or blood with monoclonal antibody(ies) binding to novel cleaved form(s) of tau proteins or neurofilament proteins described in the present application; and (c) detecting the presence and/or level of the cleaved form(s) of the tau proteins or neurofilament proteins bound to the monoclonal antibody(ies).

The method of the present invention may also include the step of comparing the amount of the cleaved form(s) of the tau proteins or neurofilament proteins bound to the monoclonal antibody(ies) in step (c) to control samples selected from the group consisting of those representing a normal undamaged axon state and those representing an axonal damage state.

The method of the present invention may be used to detect cleaved form(s) of tau proteins or neurofilament proteins. The cleaved tau protein(s) of particular interest in the present method are those having an apparent molecular weight less than 50 kDa and being in a phosphorylated or non-phosphorylated state, particularly those fragments in the range of about 30 kDa to 50 kDa. The present method also has been forced to characterize the multiple protein bands comprising these 30 kDa to 50 kDa tau protein fragments. The cleaved neurofilament proteins of particular interest in the present method occur in human CSF or blood where they demonstrate an apparent molecular weight: 1) for neurofilament-L less than 68 kDa, 2) for neurofilament-M less than 160 kDa, 3) for neurofilament-H less than 200 kDa, and for neurofilament66 less than 66 kDa.

The method of the present invention may be used to determine whether axonal damage has occurred and to what extent, and thus can be used to determine the existence or likelihood of any disease state associated with axonal damage, such as CNS injuries, including primary neuronal injuries (e.g., cortical contusion, diffuse axonal injury, subcortical gray matter injury and primary brain stem injury), primary hemorrhages (e.g., subdural hematoma, epidural hematomas, intracerebral hematoma and diffuse hemorrhages), primary vascular injuries (e.g., arterial psuedoaneurysm, arterial dissection/occlusion), dural sinus laceration/occlusion, traumatic pia-arachnoid injuries, cranial nerve injuries and secondary traumatic lesions (e.g., infarction, hypoxic injury, diffuse brain swelling/edema, secondary hemorrhage), central nervous system tumor, neurodegenerative diseases of the central nervous system including Alzheimer's disease, spinal cord injury, acute cerebral vascular accident or axonal damage following ingestion of drug(s) or poison(s).

The present invention also includes cleaved forms of tau proteins having an apparent molecular weight less than 50 kDa particularly those fragments in the range of about 30 kDa to 50 kDa, and being in a substantially isolated and/or purified form. The present invention also includes cleaved forms of neurofilament proteins in a substantially isolated form occuring in human CSF where they demonstrate an apparent molecular weight: 1) for neurofilamnent-L less than 68 kDa, 2) for neurofilament-M less than 160 kDa, 3) for neurofilament-H less than 200 kDa, and for neurofilament66 less than 66 kDa. These substances may be used as standards or controls in tests using the present invention.

Substantially isolated and/or purified MAbs raised against at least one tau protein and/or its cleaved forms, and having been screened against human CSF are also included in the present invention. As used herein, a substantially isolated or substantially purified monoclonal antibody consists of a single hybridoma clone recognizing a single protein epitope essentially free of contaminating or interfering molecules. It is preferred that such MAbs are those raised against tau protein fragments, and having been screened against human CSF, said monoclonal antibody being in a substantially isolated form, and said tau protein fragment comprising the peptide sequence including the amino acids from serine$^{199}$ to serine$^{396}$ of tau protein, and lacking the native N-terminal and C-terminal amino acids. These substances are useful in the methods of the present invention.

The present invention can also be used to ascertain or predict the severity of neurologic trauma, such as intercranial lesions, or the neurologic disease states giving rise to tau or neurofilament proteins in CSF or blood, such as those disease states discussed above and/or to ascertain or predict clinical outcome following such trauma.

DETAILED DESCRIPTION OF INVENTION

Figure 1:
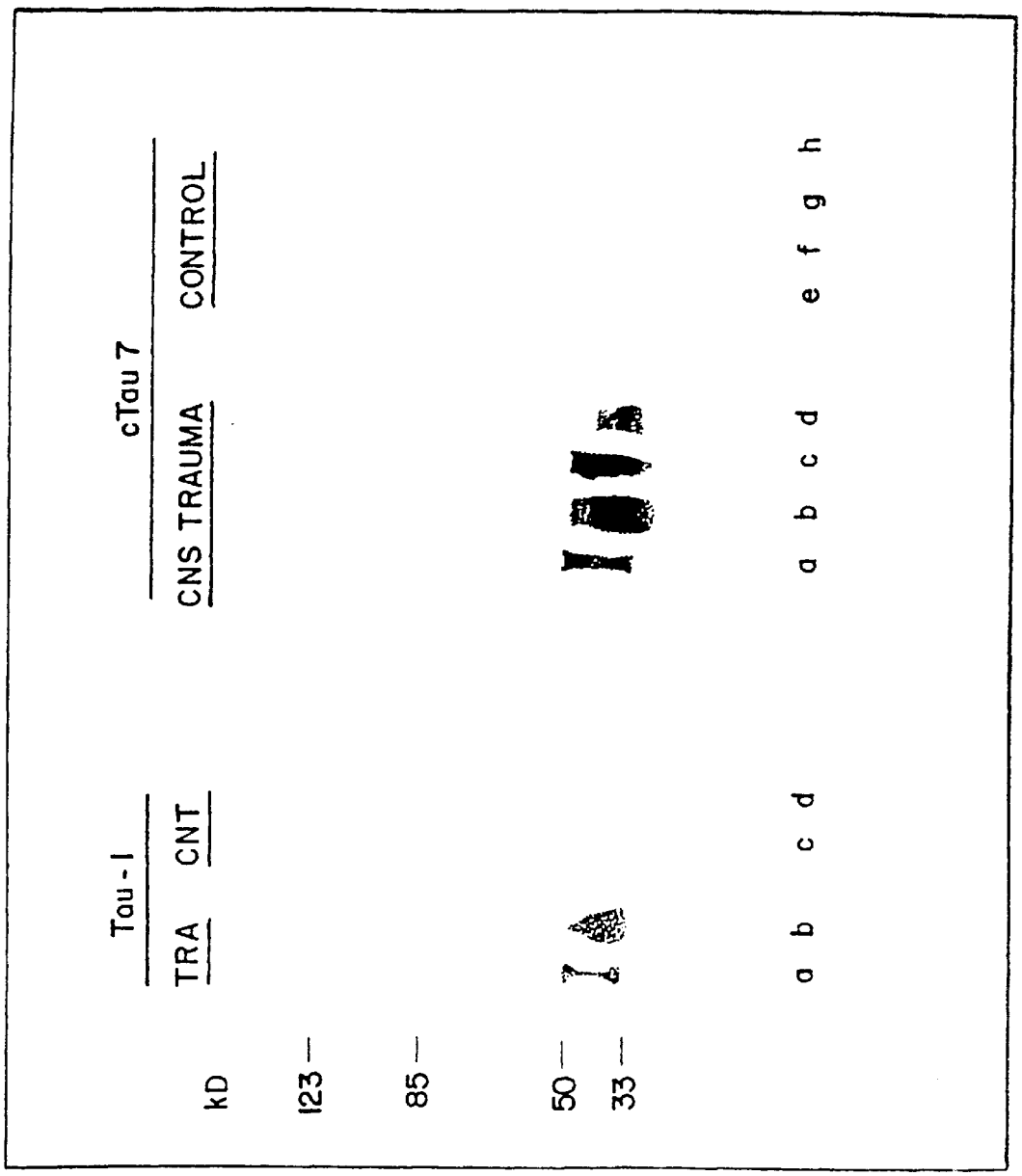
FIG. 1. Monoclonal antibodies recognizing cerebrospinal fluid cleaved tau proteins were developed by differential CSF screening. Left panel: Initial studies demonstrated that Mab Tau-1 labeled 30 kD to 50 kD CSF proteins in CNS trauma patients (TRA; lane a 50 µl CSF, lane b 10 µl CSF) but not normal controls (CNT; lane c and d both 50 µl CSF). Right panel: MAbs were developed that specifically recognized 30 kD to 50 kD CSF tau proteins employing a differential CSF screen. Hybridomas were selected that labeled CSF from CNS trauma patients (lanes a–d) but not control patients (lanes e–h). The same patient samples were run in lanes a and b in left and right panels. cTau7 lanes a and e–h 50 µl CSF, lanes b–d 10 µl CSF. Molecular weight markers shown at right.

The proteins that are useful in the present invention are a novel class of axonally-derived proteins occurring in human CSF and blood including cleaved tau proteins and cleaved neurofilament proteins. As used herein, axonally-derived proteins refer to a group of proteins that occur in axons of CNS neurons and are released into the extracellular space during degeneration of said axons. As used herein, the term full length tau refers to any of the six non- cleaved isoforms of this protein that demonstrate an apparent molecular weight of 48 to 68 kDa and whose genomic and amino acid sequences are described in Goedert et al. (1989). The class of novel cleaved tau proteins that are useful in the invention were discovered in human cerebrospinal fluid and have been purified. These novel cleaved tau proteins may be distinguished from previously described full length tau proteins, in that they: 1) have reduced apparent molecular weights in comparison to full length tau, 2) are comprised of the interior portion of the tau sequence that includes ser$^{199}$ to ser$^{396}$ of tau, and 3) lack the N-terminal and C-terminal amino acids of tau. As used herein, the term neurofilament-L refers to a protein with an apparent molecular weight of 68 kDa and whose genomic and amino acid sequences are described in Julien et al. (1987). As used herein, the term neurofilament-M refers to a protein with an apparent molecular weight of 160 kDa and whose genomic and amino acid sequences are described in Myers et al. (1987). As used herein, the term neurofilament-H refers to a protein with an apparent molecular weight of 200 kDa and whose genomic and amino acid sequences are described in Lees et al. (1988). As used herein, the term neurofilament66 refers to a protein with an apparent molecular weight of 66 kDa and whose genomic and amino acid sequences are described in Chan and Chiu (1995).

Antibodies specifically reactive with the novel cleaved tau proteins are included within the scope of the invention. A "specifically reactive" antibody is one that is capable of binding with a particular molecule to thereby couple said molecule to the antibody. The term "epitope" refers to that portion of a hapten that can be recognized and bound by an antibody. The present disclosure indicates that the antigen employed for monoclonal antibody production, a cleaved form of tau found in human cerebrospinal fluid, possesses more than one epitope. An antigen is a molecule capable of inducing an animal to produce an antibody capable of binding to an epitope of that antigen. The specific reaction referred to above is meant to indicate that an antibody will bind with a significantly higher affinity to its corresponding antigen as opposed to the multitude of other antigens occurring in the human body. For example, there is provided by this invention several MAbs (i.e. cTau-7, cTau-8 and cTau-12) raised against the cleaved form of tau found in CSF. These cTau antibodies demonstrated sufficiently higher affinity for cleaved tau than for full length tau such that selective immunolabeling of cleaved tau occurred with equivalent protein loads on Western blots.

In particular, the invention includes a method for detecting and quantitating an axonally- derived protein in a human subject, comprising:

(a) contacting a blood sample from a human subject that is suspected of containing detectable levels of an axonally-derived protein with a molecule capable of binding to the axonally-derived protein; and (b) detecting the molecule bound to the axonally-derived protein.

The invention additionally includes the method as above, wherein the binding molecule is selected from the group consisting of:

(a) an antibody substantially free of natural impurities;

(b) a monoclonal antibody; and (c) a fragment of (a) or (b).

The invention additionally includes the method as above, wherein the detecting molecule is detectably labeled and where a combination of such binding molecules is used.

The invention additionally includes a method for determining the presence of a condition in a human subject, said condition including, but not limited to, the group consisting of Alzheimer's Disease, the presence of neuroectodermal tumors, the presence of malignant astrocytomas, and the presence of gliomas.

The invention additionally includes a method of diagnosing the presence of neurological disease in a human subject suspected of having neurological disease, which comprises:

(a) incubating a biological sample from said subject suspected of containing an axonally-derived protein with a molecule capable of identifying an axonally-derived protein; and (b) detecting the molecule, which is bound in the sample, wherein the detection indicates that the subject has neurological disease.

The invention additionally includes a method of diagnosing the presence of neuroectodermal tumors in a human subject suspected of having neuroectodermal tumors which comprises:

(a) incubating a biological sample from said subject suspected of containing an axonally-derived protein with a molecule capable of identifying an axonally-derived protein; and (b) detecting the molecule, which is bound in the sample, wherein the detection indicates that the subject has neuroectodermal tumors.

Immunoassays

Antibodies directed against an axonally-derived protein can be used, as taught by the present invention, to detect and diagnose neurological disease. Various histological staining methods, including immunohistochemical staining methods, may also be used effectively according to the teaching of the invention. Silver stain is but one method of visualizing axonally-derived protein. Other staining methods useful in the present invention will be obvious to the artisan, the determination of which would not involve undue experimentation.

One screening method for determining whether a given compound is an axonally-derived protein functional derivative comprises, for example, immunoassays employing radioimmunoassay (RIA) or enzyme-linked immunosorbent assay (ELISA) methodologies, based on the production of specific antibodies (monoclonal or polyclonal) to an axonally-derived protein. Venipuncture (blood), spinal tap (cerebral spinal fluid (CSF)), urine and other body secretions, such as sweat and tears, are used as biological samples. For example, in one form of RIA, the substance under test is mixed with diluted antiserum in the presence of radiolabeled antigen. In this method, the concentration of the test substance will be inversely proportional to the amount of labeled antigen bound to the specific antibody and directly related to the amount of free labeled antigen. Other suitable screening methods will be readily apparent to those of skill in the art.

The present invention also relates to methods of detecting an axonally-derived protein or functional derivatives in a sample or subject. For example, antibodies specific for an axonally- derived protein, or a functional derivative, may be detectably labeled with any appropriate marker, for example, a radioisotope, an enzyme, a fluorescent label, a paramagnetic label, or a free radical.

Alternatively, antibodies specific for an axonally-derived protein, or a functional derivative, may be detectably labeled with DNA by the technique of immunopolymerase chain reaction. The polymerase chain reaction (PCR) procedure amplifies specific nucleic acid sequences through a series of manipulations including denaturation, annealing of oligonucleotide primers, and extension of the primers with DNA polymerase (see, for example, U.S. Pat. No. 4,683,202).

Various amounts of the test material can be immobilized on the surface of microtiter wells. The wells are subsequently incubated with an axonally-derived protein monoclonal antibody, washed, and then incubated with biotinylated axonally-derived protein DNA molecules that have been conjugated to streptavidin-protein chimera (Id.). This chimera binds biotin (via the streptavidin moiety) and the Fc portion of an immunoglobulin G molecule. The wells are then washed to remove unbound conjugates. Any axonally-derived protein present in the test material will be bound by the axonally-derived protein monoclonal antibody, which in turn, is bound by the protein A moiety of the biotinylated axonally-derived protein DNA-streptavidin-protein A conjugate. Then, the axonally-derived protein DNA sequences are amplified using PCR. The PCR products are then analyzed by agarose gel electrophoresis after staining with ethidium bromide.

Methods of making and detecting such detectably labeled antibodies or their functional derivatives are well known to those of ordinary skill in the art. The term "antibody" refers both to monoclonal antibodies, which are a substantially homogeneous population and to polyclonal antibodies, which are heterogeneous populations. Polyclonal antibodies are derived from the sera of animals immunized with an antigen. Monoclonal antibodies (MAbs) to specific antigens may be obtained by methods known to those skilled in the art. See, for example, U.S. Pat. No. 4,376,110. Such antibodies may be of any immunoglobulin class including IgG, IgM, IgE, IgA, IgD and any subclass thereof. The term "antibody" is also meant to include both intact molecules as well as fragments thereof, such as, for example, Fab and F(ab')2, which are capable of binding antigen. Fab and F(ab')2 fragments lack the Fc fragment of intact antibody, clear more rapidly from the circulation, and may have less non-specific tissue binding than an intact antibody.

It will be appreciated that Fab and F(ab')2 and other fragments of the antibodies useful in the present invention may be used for the detection and quantitation of an axonally-derived protein according to the methods disclosed herein in order to detect and diagnose neurological disease in the same manner as an intact antibody. Such fragments are typically produced by proteolytic cleavage, using enzymes such as papain (to produce Fab fragments) or pepsin (to produce F(ab')2 fragments).

An antibody is said to be "capable of binding" a molecule if it is capable of specifically reacting with the molecule to thereby bind the molecule to the antibody. The term "epitope" is meant to refer to that portion of any molecule capable of being bound by an antibody that can also be recognized by that antibody. Epitopic determinants usually consist of chemically active surface groupings of molecules such as amino acids or sugar side chains and have specific three dimensional structural characteristics as well as specific charge characteristics.

An "antigen" is a molecule capable of being bound by an antibody that is additionally capable of inducing an animal to produce antibody capable of binding to an epitope of that antigen. An antigen may have one, or more than one epitope. The specific reaction referred to above is meant to indicate that the antigen will react, in a highly selective manner, with its corresponding antibody and not with the multitude of other antibodies that may be evoked by other antigens.

The antibodies, or fragments of antibodies, useful in the present invention may be used to quantitatively or qualitatively detect the presence of cells that contain the axonally-derived protein antigens. Thus, the antibodies (or fragments thereof) useful in the present invention may be employed histologically to detect or visualize the presence of an axonally-derived protein.

Such an assay for an axonally-derived protein typically comprises incubating a biological sample from said subject suspected of having such a condition in the presence of a detectably labeled binding molecule (e.g., antibody) capable of identifying an axonally-derived protein, and detecting said binding molecule which is bound in a sample.

Thus, in this aspect of the invention, a biological sample may be treated with nitrocellulose, or other solid support that is capable of immobilizing cells, cell particles or soluble proteins. The support may then be washed with suitable buffers followed by treatment with the detectably labeled axonally-derived protein-specific antibody. The solid phase support may then be washed with the buffer a second time to remove unbound antibody. The amount of bound label on said solid support may then be detected by conventional means.

By "solid phase support" is intended any support capable of binding antigen or antibodies. Well-known supports, or carriers, include glass, polystyrene, polypropylene, polyethylene, dextran, nylon, amylases, natural and modified celluloses, polyacrylamides, agaroses, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will note many other suitable carriers for binding monoclonal antibody or antigen, or will be able to ascertain the same by use of routine experimentation.

One embodiment for carrying out the diagnostic assay of the present invention on a biological sample containing an axonally-derived protein, comprises:
(a) contacting a detectably labeled axonally-derived protein-specific antibody with a solid support to effect immobilization of said axonally-derived protein-specific antibody or a fragment thereof;
(b) contacting a sample suspected of containing an axonally-derived protein with said solid support;
(c) incubating said detectably labeled axonally-derived protein-specific antibody with said support for a time sufficient to allow the immobilized axonally-derived protein-specific antibody to bind to the axonally-derived protein;
(d) separating the solid phase support from the incubation mixture obtained in step (c); and
(e) detecting the bound label and thereby detecting and quantifying axonally-derived protein.

Alternatively, labeled axonally-derived protein-specific antibody/axonally-derived protein complexes in a sample may be separated from a reaction mixture by contacting the complex with an immobilized antibody or protein which is specific for an immunoglobulin, e.g., Staphylococcus protein A, Staphylococcus protein G, anti-IgM or anti-IgG antibodies. Such anti-immunoglobulin antibodies may be polyclonal, but are preferably monoclonal. The solid support may then be washed with a suitable buffer to give an immobilized axonally-derived protein/labeled axonally-derived protein-specific antibody complex. The label may then be detected to give a measure of an axonally-derived protein.

This aspect of the invention relates to a method for detecting an axonally-derived protein or a fragment thereof in a sample comprising:
(a) contacting a sample suspected of containing an axonally-derived protein with an axonally-derived protein-specific antibody or fragment thereof which binds to axonally-derived protein; and
(b) detecting whether a complex is formed.

The invention also relates to a method of detecting an axonally-derived protein in a sample, further comprising:
(c) contacting the mixture obtained in step (a) with an Fc binding molecule, such as an antibody, Staphylococcus protein A, or Staphylococcus protein G, which is immobilized on a solid phase support and is specific for the axonally-derived protein-specific antibody to give an axonally-derived protein/axonally-derived protein-specific antibody immobilized antibody complex;
(d) washing the solid phase support obtained in step (c) to remove unbound axonally-derived protein/axonally-derived protein-specific antibody complex;
(e) and detecting the label bound to said solid support.

Of course, the specific concentrations of detectably labeled antibody and axonally-derived protein, the temperature and time of incubation, as well as other assay conditions may be varied, depending on various factors including the concentration of an axonally-derived protein in the sample, the nature of the sample, and the like. The binding activity of a given lot of anti-axonally-derived protein antibody may be determined according to well-known methods. Those skilled in the art will be able to determine operative and optimal assay conditions for each determination by employing routine experimentation.

Other such steps as washing, stirring, shaking, filtering and the like may be added to the assays as is customary or necessary for the particular situation.

One of the ways in which the axonally-derived protein-specific antibody can be detectably labeled is by linking the same to an enzyme. This enzyme, in turn, when later exposed to its substrate, will react with the substrate in such a manner as to produce a chemical moiety that can be detected, for example, by spectrophotometric, fluorometric or by visual means. Enzymes which can be used to detectably label the axonally-derived protein-specific antibody include, but are not limited to, malate dehydrogenase, staphylococcal nuclease, delta-V-steroid isomerase, yeast alcohol dehydrogenase, alpha -glycerophosphate dehydrogenase, triose phosphate isomerase, horseradish peroxidase, alkaline phosphatase, asparaginase, glucose oxidase, beta -galactosidase, ribonuclease, urease, catalase, glucose-VI-phosphate dehydrogenase, glucoamylase and acetylcholinesterase.

Detection may be accomplished using any of a variety of immunoassays. For example, by radioactively labeling the axonally-derived protein-specific antibodies or antibody fragments, it is possible to detect axonally-derived protein through the use of radioimmunoassays.

The radioactive isotope can be detected by such means as the use of a gamma counter or a scintillation counter or by autoradiography. Isotopes that are particularly useful for the purpose of the present invention are: 3H, 125I, 131I, 35S, 14C, and preferably 125I.

It is also possible to label the axonally-derived protein-specific antibody with a fluorescent compound. When the fluorescently labeled antibody is exposed to light of the proper wavelength, its presence can then be detected due to fluorescence. Among the most commonly used fluorescent labelling compounds are fluorescein isothiocyanate, rhodamine, phycoerytherin, phycocyanin, allophycocyanin, o-phthaldehyde and fluorescamine.

The axonally-derived protein-specific antibody can also be detectably labeled using fluorescence emitting metals such as 152Eu, or others of the lanthanide series. These metals can be attached to the axonally-derived protein-specific antibody using such metal chelating groups as diethylenetriaminepentaacetic acid (DTPA) or ethylenediaminetetraacetic acid (EDTA).

The axonally-derived protein-specific antibody also can be detectably labeled by coupling it to a chemiluminescent compound. The presence of the chemiluminescent-tagged axonally-derived protein-specific antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

The axonally-derived protein-specific antibody may also be labeled with biotin and then reacted with avidin. A biotin-labeled DNA fragment will be linked to the axonally-derived protein-biotinylated monoclonal antibody by an avidin bridge. axonally-derived protein molecules are then detected by polymerase chain reaction (PCR) amplification of the DNA fragment with specific primers.

Likewise, a bioluminescent compound may be used to label the axonally-derived protein-specific antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Detection of the axonally-derived protein-specific antibody may be accomplished by a scintillation counter, for example, if the detectable label is a radioactive gamma emitter, or by a fluorometer, for example, if the label is a fluorescent material. In the case of an enzyme label, the detection can be accomplished by calorimetric methods that employ a substrate for the enzyme. Detection may also be accomplished by visual comparison of the extent of enzymatic reaction of a substrate in comparison with similarly prepared standards.

The detection of foci of such detectably labeled antibodies is indicative of a disease or dysfunctional state as previously described. For the purposes of the present invention, the axonally-derived protein that is detected by this assay may be present in a biological sample. Any sample containing an axonally-derived protein can be used. However, one of the benefits of the present diagnostic invention is that invasive tissue removal may be avoided. Therefore, preferably, the sample is a biological solution such as, for example, cerebrospinal fluid, amniotic fluid, blood, serum, urine and the like. However, the invention is not limited to assays using only these samples, it being possible for one of ordinary skill in the art to determine suitable conditions that allow the use of other samples.

For example, the three-site monoclonal antibody-based immunoradiometric assays (M-IRMA) may be used to measure axonally-derived protein levels in a biological fluid, such as CSF, blood, plasma or serum. While it is possible to obtain, by spinal tap, on a routine basis, CSF from individuals suspected of having neurological disease, it is an intrusive method. Thus, the diagnosis of neurological disease can be established by a simple, non-invasive blood immunoassay that reveals axonally-derived protein levels greatly increased over normal levels.

There are many different in vivo labels and methods of labeling known to those of ordinary skill in the art. Examples of the types of labels that can be used in the present invention include radioactive isotopes and paramagnetic isotopes. Those of ordinary skill in the art will know of other suitable labels for binding to the antibodies used in the invention, or will be able to ascertain such, using routine experimentation. Furthermore, the binding of these labels to the antibodies can be done using standard techniques common to those of ordinary skill in the art.

An important factor in selecting a radionuclide for in vivo diagnosis is that the half-life of a radionuclide be long enough so that it is still detectable at the time of maximum uptake by the target, but short enough so that deleterious radiation upon the host is minimized. Ideally, a radionuclide used for in vivo imaging will lack a particulate emission, but produce a large number of photons in the 140–200 keV range, which maybe readily detected by conventional gamma cameras.

For in vivo diagnosis radionuclides may be bound to antibody either directly or indirectly by using an intermnediary functional group. Intermediary functional groups that are often used in binding radioisotopes that exist as metallic ions to immunoglobulins are DTPA and EDTA. Typical examples of ions that can be bound to immunoglobulins are 99mTc, 123I, 111In, 131I, 97Ru, 67Cu, 67Ga, 125I, 68Ga, 72As, 89Zr, and 201T1.

For diagnostic in vivo imaging, the type of detection instrument available is a major factor in selecting a given radionuclide. The radionuclide chosen must have a type of decay that is detectable for a given type of instrument. In general, any conventional method for visualizing diagnostic imaging can be utilized in accordance with this invention. For example, PET, gamma, beta, and MRI detectors can be used to visualize diagnostic imagining.

The antibodies useful in the invention can also be labeled with paramagnetic isotopes for purposes of in vivo diagnosis. Elements that are particularly useful, as in Magnetic Resonance Imaging (MRI), include 157Gd, 55Mn, 162Dy, and 56Fe.

The antibodies (or fragments thereof) useful in the present invention are also particularly suited for use in in vitro immunoassays to detect the presence of an axonally-derived protein in body tissue, fluids (such as CSF, blood, plasma or serum), or cellular extracts. In such immunoassays, the antibodies (or antibody fragments) may be utilized in liquid phase or, preferably, bound to a solid-phase carrier, as described above.

Those of ordinary skill in the art will know of other suitable labels that may be employed in accordance with the present invention. The binding of these labels to antibodies or fragments thereof can be accomplished using standard techniques commonly known to those of ordinary skill in the art. Coupling techniques mentioned in the latter are the glutaraldehyde method, the periodate method, the dimaleimide method, the m-maleimidobenzyl-N-hydroxysuccinimide ester method, all of which methods are incorporated by reference herein.

Removing a histological specimen from a patient, and providing the combination of labeled antibodies of the present invention to such a specimen may accomplish in situ detection. The antibody (or fragment) is preferably provided by applying or by overlaying the labeled antibody (or fragment) to a biological sample. Through the use of such a procedure, it is possible to determine not only the presence of an axonally-derived protein, but also the distribution of an axonally-derived protein on the examined tissue. Using the present invention, those of ordinary skill will readily perceive that any of a wide variety of histological methods (such as staining procedures) can be modified in order to achieve such in situ detection.

The binding molecules of the present invention may be adapted for utilization in an immunometric assay, also known as a "two-site" or "sandwich" assay. In a typical immunometric assay, a quantity of unlabeled antibody (or fragment of antibody) is bound to a solid support that is insoluble in the fluid being tested (i.e., CSF, blood, plasma or serum) and a quantity of detectably labeled soluble antibody is added to permit detection and/or quantitation of the ternary complex formed between solid-phase antibody, antigen, and labeled antibody.

Typical, and preferred, immunometric assays include "forward" assays in which the antibody bound to the solid phase is first contacted with the sample being tested to extract the antigen from the sample by formation of a binary solid phase antibody-antigen complex. After a suitable incubation period, the solid support is washed to remove the residue of the fluid sample, including unreacted antigen, if any, and then contacted with the solution containing an unknown quantity of labeled antibody (which functions as a "reporter molecule"). After a second incubation period to permit the labeled antibody to complex with the antigen bound to the solid support through the unlabeled antibody, the solid support is washed a second time to remove the unreacted labeled antibody. This type of forward sandwich assay may be a simple "yes/no" assay to determine whether antigen is present or may be made quantitative by comparing the measure of labeled antibody with that obtained for a standard sample containing known quantities of antigen.

In another type of "sandwich" assay, which may also be useful with the antigens of the present invention, the so-called "simultaneous" and "reverse" assays are used. A simultaneous assay involves a single incubation step as the antibody bound to the solid support and labeled antibody are both added to the sample being tested at the same time. After the incubation is completed, the solid support is washed to remove the residue of fluid sample and uncomplexed labeled antibody. The presence of labeled antibody associated with the solid support is then determined as it would be in a conventional "forward" sandwich assay.

In the "reverse" assay, stepwise addition first of a solution of labeled antibody to the fluid sample followed by the addition of unlabeled antibody bound to a solid support after a suitable incubation period is utilized. After a second incubation, the solid phase is washed in conventional fashion to free it of the residue of the sample being tested and the solution of unreacted labeled antibody. The determination of labeled antibody associated with a solid support is then determined as in the "simultaneous" and "forward" assays.

The above-described in vitro or in vivo detection methods may be used in the detection and diagnosis of neurological disease without the necessity of removing tissue. Such detection methods may be used to assist in the determination of the stage of neurological deterioration in neurological disease by evaluating and comparing the concentration of an axonally-derived protein in the biological sample.

As used herein, an effective amount of a diagnostic reagent (such as an antibody or antibody fragment) is one capable of achieving the desired diagnostic discrimination and will vary depending on such factors as age, condition, sex, extent of disease of the subject, counter-indications, if any, and other variables to be adjusted by the physician. The amounts of such materials that are typically used in a diagnostic test are generally between 0.1 to 5 mg, and preferably between 0.1 to 0.5 mg.

The assay of the present invention is also ideally suited for the preparation of a kit. Such a kit may comprise a carrier means being compartmentalized to receive in close confinement therewith one or more container means such as vials, tubes and the like, each of said container means comprising the separate elements of the immunoassay.

For example, there may be a container means containing a first antibody immobilized on a solid phase support, and a further container means containing a second detectably labeled antibody in solution. Further container means may contain standard solutions comprising serial dilutions of the axonally-derived protein to be detected. The standard solutions of an axonally-derived protein may be used to prepare a standard curve with the concentration of axonally-derived protein plotted on the abscissa and the detection signal on the ordinate. The results obtained from a sample containing an axonally-derived protein may be interpolated from such a plot to give the concentration of the axonally-derived protein.

EXAMPLE

Purification, Characterization and Measurement of Human Cerebrospinal Fluid Cleaved Tau Proteins in Patients with Axonal Degeneration Summary of Example Tau proteins are structural axonal proteins associated with microtubule stabilization. Under normal conditions tau is a non-released intraneuronal protein, however, the disclosure teaches that tau gains access to the CSF during axon degeneration. As described in the present disclosure, the cleaved form of tau proteins found in human CSF during axon degeneration were purified, characterized and MAbs that selectively bind to this novel cleaved form of tau developed. These monoclonals were employed to develop a sandwich ELISA for measuring CSF cleaved tau. Employing this ELISA, patients with axonal degeneration demonstrated CSF cleaved tau levels 10,000 times higher than patients without axonal degeneration; no overlap in CSF cleaved tau levels between the two groups of patients was observed.

We have previously disclosed that cerebrospinal fluid (CSF) levels of cleaved-tau are elevated during clinical states associated with neuronal degeneration (Zemlan F. P., Rosenberg W. S., Luebbe P. A., Campbell T. A.; Dean G. E., Weiner N. E., Cohen J. A., Rudick R. A. and Woo D. (1999) Quantification of axonal damage in traumatic brain injury: Affinity purification and characterization of cerebrospinal fluid tau proteins. *J. Neurochemistry* 72, 741–750). It would not be expected that cleaved-tau levels would also be elevated in serum in these patients as blood is compartmentalized from CSF by the blood-brain-barrier. The fundamental basis for compartmentalization between blood and CSF is the tight junctions that exist between endothelial cells that comprise the blood-brain-barrier (Saunders NR, Habgood MD and Dziegielewska. (1999) Barrier mechanisms in the brain, I. Adult brain. *Clin. Exp. Pharmacol. Physiol.* 26: 11–19). These tight junctions exclude all but the smallest proteins (less than 5 kDa molecular weight). As cleaved-tau is much larger, demonstrating an average molecular weight of 40 kDa, one skilled-in-the-art would not expect to find cleaved-tau in serum of these patients. Surprisingly, when we examined patients undergoing neuronal degeneration resulting from sever head injury or stroke, we found elevated levels of serum cleaved-tau in both groups of patients (Table 2). The cause of this unexpected elevation in both CSF and serum cleaved-tau is unknown, however, the elevation in serum cleaved-tau may be related to disruption of the blood-brain-barrier that is disease-associated.

Materials and Methods

CSF Samples

CSF samples were collected under an approved protocol from the University of Cincinnati Institutional Review Board. CSF was collected from hospitalized patients with severe brain injury (Glasgow Coma Scale <10) resulting from trauma or intracranial aneurysmal rupture via intraventricular catheters. CSF was collected by lumbar puncture from control patients. CSF samples were centrifuged at 13,000 g for 15 min and stored at −70° C. until use.

Serum Samples Cleaved-tau serum sandwich ELISA. Measurement of patient serum cleaved-tau employs our previously characterized ELISA which utilizes catalyzed reporter deposition for increased sensitivity (Zemlan et al, 1999). This ELISA employs three MAbs (7A5, 8A12 and 12B2) that specifically recognize the cleaved form of MAP-tau present in CSF and serum. Briefly, serum was collected from patients with severe or moderate head injury, as well as, neurologic and non-neurologic controls in "marble top" serum tubes containing a coagulant and separator. Samples were centrifuged for 15 minutes at 14,000 rpm in a clinical centrifuge to separate serum from blood elements, and serum stored at −80 ° C. until assay. Immulon 2 plates are coated with affinity purified Mab 12B2 (100 µl/well, 5 ug/ml) for 1 h and overcoated overnight with 5% nonfat dry milk and 0.5% gelatin in Tris buffered saline (TBS). Plates are washed with 0.1% Tween in TBS (TBST), and serial dilutions of patient serum (80 µl serum, 8 µl serum, 0.8 µl) added in triplicate, incubated for 1 hr and then washed with TBST. 100 µl/well of HRP-conjugated 7A5 and 8A12 diluted 1:2,000 is added for 1 hr, plates washed with TBST and 100 µl/well of a 3 µg/ml solution of biotin-tyramine in 50 mM Tris-HCl, 0.001% $H_2O_2$ (pH 8.0) added for 15 min. Color is developed with Vector ABC-AP using nitrophenylphosphate as substrate and read at 405 nm. Affinity purified human tau is employed as standard. Negative controls include exclusion of 12B2, deletion of sample, or deletion biotinylated 7A5 and 12B2 from the assay. The sensitivity of this ELISA is 30 µg per well and demonstrates an intra-assay variation of less than 7% and an inter-assay variation less than 10%.

Protein Purification and Expression

Tau purification, dephosphorylation and digestion. Tau was purified using a procedure modified from Nukina et al. (1987). Briefly, post mortem human brains were homogenized in a volume 2.5 times the weight in 50 mM Tris-HCl (pH 6.8), 0.3 M NaCl, 1% β-mercaptoethanol (BME), 1 mM PMSF and 5 µM leupeptin. The homogenate was centrifuged at 30,000×g for 5 min at 4° C. The supernatant was incubated on ice and the pellet homogenized a second time in a volume 2.5 times the weight with 50 mM Tris-HCl (pH 9.2), 0.3 M NaCl, 1% BME. The homogenate was then centrifuged at 4° C. for 5 min at 30,000×g. The supernatants were combined and boiled for 10 min. The samples were then spun for 30 minutes at 30,000×g at 4° C. The samples were dialyzed overnight against 50 mM Tris-HCl before examination by SDS-PAGE. Tau antigen was prepared by running the tau preparation on 10% SDS-polyacrylamide curtain gels. Proteins with molecular weights of 30 kDa to 80 kDa were excised and electroeluted in a Schleicher & Schuell (Keene, N.H.) Elutrap device containing 40 mM Tris-borate buffer (pH 8.64) and 0.8% SDS, then dialyzed against 50 mM Tris-HCl prior to injection. Brain and CSF tau proteins were dephosphorylated overnight at 37° C. in 50 mM Tris-HCl (pH 8.0) with or without 1 U/ml bacterial alkaline phosphatase (BAP; Sigma Chemical Co.). The effect of BAP treatment on Mab binding was assessed by solid phase ELISA. Wells were coated with 300 ng of tau, blocked and washed, and primary antibody added for 1 hr and assayed as described below. For epitope mapping studies, tau samples were digested in 200 µl of 70% formnic acid containing 50 mg/ml cyanogen bromide (CNBr) solution and incubated overnight at room temperature. Samples were washed twice with 1 ml $ddH_2O$ and evaluated on 15% SDS-PAGE gels.

Purification of microtubules. Tubulin was purified from rat brain and microtubules assembled in the presence of taxol (Schiff et al., 1979; Vallee, 1982). Microtubule-associated proteins (MAPs) were dissociated from the microtubules by suspending the microtubule pellet (600 µg) in assembly buffer (40 µM taxol in 0.1 M PIPES, 1.0 mM EGTA, 1.0 M $MgSO_4$ and 1.0 mM GTP,) and NaCl added to a final concentration of 0.35 M. CSF and brain samples were incubated with shaking for 10 min at 37° C. and centrifuged at 30,000×g for 25 min. After repeated salt extractions (3×), all MAPs had been removed from the microtubule samples as judged by Western blots of the third supernatant probed with BYA.

MAP purification. NaCl was removed from the above microtubule pellet (600 µg) by washing in 1.3 ml of assembly buffer. Microtubules were pelleted at 30,000×g for 25 min; CSF or human heat-stable proteins containing tau and 1.3 ml assembly buffer were added to the pellet, incubated for 10 min at 37° C., and centrifuged at 30,000×g for 25 min. Proteins not bound to microtubules were removed by two cycles of washing (1.3 ml assembly buffer, incubation for 10 min at 37° C., centrifugation at 30,000×g for 25 min). Microtubule bound proteins were dissociated by the addition of 0.5 ml of assembly buffer with 0.35 M NaCl to the washed microtubule pellet. Following incubation for 10 min at 37° C. the sample was dialyzed against 50 mM Tris-HCl and analyzed by immunoblotting.

Recombinant tau. Recombinant human tau was produced using the previously described pET-n123c and pET-n1234c plasmids expressed in the BL21(DE3) expression vector (Lee and Rook, 1992). The plasmids were the generous gift of Dr. Gloria Lee. Plasmid pET-n123c codes for the 352 amino acid three repeat form of tau while plasmid pET-n1234c codes for the 383 amino acid four repeat form of tau containing exon 10. Following expression tau was purified as above and was estimated to be approximately 90% pure as judged by Commassie Blue stained SDS-PAGE.

Monoclonal Antibody Production

Monoclonal human cleaved tau antibodies. Female Balb/C mice were injected interperitoneally with 100 µg of the antigen preparation suspended in an equal volume of Freund's complete adjuvant (Sigma, St. Louis, Mo.). Boosts were performed at two week intervals with 100 µg of the antigen suspended in incomplete Freund's adjuvant (Sigma). Mice were bled prior to each boost and sera titered by ELISA. MAbs were produced as previously described (Kohler and Milstein, 1975). Briefly, $1.8 \times 10^8$ spleen cells were mixed with $3.6 \times 10^7$ NS1/1-Ag-4 mouse myeloma cells. Fusion was induced by addition of 38% polyethylene glycol 1550. Cells were washed with DMEM (Gibco BRL, Gaithersburg, Md.) and resuspended in Super DMEM (Gibco BRL) containing 14% fetal calf serum and HAT (Sigma). Cells were dispersed in 96-well microtiter plates coated with a mouse splenocyte feeder layer. Supernatants were screened after plating against CSF from CNS trauma patients or controls by ELISA and Western blot. Colonies that produced supernatant found to react with CSF from CNS trauma patients but not control CSF were expanded and cloned by limiting dilution. To insure isolation of monoclonal hybridomas, cloning was repeated until 100% of the wells showed specific Mab production. At the end of this process, three MAbs, designated cTau7, cTau8 and cTau12 were recovered.

Ascites production. Male Balb/C mice were primed by IP injection of 0.5 ml pristane (Sigma) followed 14 days later by injection of 106 hybridoma cells. After seven days, the peritoneal cavities were tapped. Ascites fluids were titered, pooled by hybridoma and stored at −20° C. To ensure establishment of stable cell lines, hybridomas were passed twice through pristane primed mice. Following each passage, hybridomas were recloned. Stability was defined as 100% of hybridoma supernatants exhibiting immunoreactivity against antigen by ELISA. Stable hybridomas were then injected into mice and ascites collected for Mab purification (below).

Mab purification and tau affinity purification. One ml of ascites was diluted 1:1 with 50 mM sodium acetate (pH 5.0) and applied to 2 ml of equilibrated Protein G sepharose. After washing, MAbs were eluted with Gentle Ag/Ab Elution Buffer (Pierce, Rockford, Ill.) and desalted over sepharose G-25 (2SQ-B, Isolab, Inc., Akron, Ohio). Mab purity was confirmed by isoelectric focusing using Resolve™ agarose EEF gels (Isolab, Akron, Ohio) and SDS-PAGE. Purified MAbs 7A5, 8A12 and 12B2 were used to affinity purify human tau using Protein G-agarose (Boehringer Mannheim, Germany) as specified by the manufacturer. Purified MAbs were conjugated to horseradish peroxidase (HRP; Finnsugar) as described in Boorsma and Kalsbeek (1975). A checkerboard titration was performed to determine the optimal conjugate dilution for ELISA and immunoblot studies.

Antibodies

MAbs PHF-1 (IgG, 1:500) and Alz50(IgM, 1:10) both raised against a PHF preparation (Wolozin et al., 1986; Greenberg et al., 1992) were the generous gift of Dr. Peter Davies. Mab SMI33 (IgM, 1:750) that recognizes non-phosphorylated $ser^{235}$ of tau (Lichtenberg-Kraag et al., 1992) was purchased from Sternberger Monoclonals Inc (Baltimore, Md.). Polyclonal antibody BYA-1074 (1:1,000) raised against bovine tau (Kosik et al., 1989) and tau Mab Tau-1 (IgG, 1:500) that recognizes non-phosphorylated $ser^{199}$ of tau (Liu et al., 1993) were purchased from Accurate Chemical & Scientific Corp. (Westbury, N.Y.). Polyclonal antibody Alz5 (1:300) was raised against a synthetic peptide corresponding to the C-terminal 13 amino acids of tau (Caputo et al., 1992).

Immunoblotting CSF or non-digested brain proteins were run on 10% SDS-polyacrylamide gels (Laemmli, 1970) and transferred electrophoretically to nitrocellulose (BA-S 85, Schleicher & Schuell, Keene, N.H.) as described by Towbin (1979). Nonspecific binding was blocked with 5% BSA in TBST (0.1 M Tris-HCl, 0.9% NaCl, with 0.1% (v/v) Tween 20) for 1 hr. The membrane was washed for 30 minutes in TBST, incubated with primary antibody for 1 hr, and blocked in 5% nonfat dry milk in TBST for 15 minutes. After washing (3 times in TBST), a 1:200 dilution of biotinylated secondary antibody (Vector Laboratories, Burlingame, Calif.) in TBST was added for 30 minutes, the membrane washed and then transferred to Vectastain ABC-peroxidase (Vector Laboratories) in TBST for 30 minutes. The blot was washed and transferred to a substrate solution of diaminobenzidine tetrahydrochloride dehydrate in phosphate-buffered saline (PBS) with 1% $NiCl_2$ and 1% $CoCl_2$. MAbs cTau7, cTau8 and cTau12 were diluted 1:1, 000 for immunoblots.

Enzyme-Linked Immunosorbent Assay

Tau sandwich ELISA. Immulon 2 plates were coated with affinity purified Mab cTau12 (100 μl/well, 5 μg/ml) for 1 h and overcoated overnight with 5% nonfat dry milk and 0.5% gelatin in TBS. Plates were washed with TBST, 100 μl/well of affinity purified tau was added (27 pg to 1,720 pg), the plates incubated for 1 h and then washed with TBST. A 1:1 mixture of HRP-conjugated MAbs cTau7 and cTau8 (100 μl/well, 1:2,000) was added, and the plates incubated for 1 h and washed with TBST. Biotin-tyramine (100 μl, 3 μg/ml in 50 mM Tris-HCl, 0.001% $H_2O_2$, pH 8.0) was added for 15 min and plates washed (Bobrow et al, 1989). Color was developed with Vector ABC-AP using nitrophenylphosphate as substrate and read at 405 nm. Negative controls included exclusion of cTau 12, deletion of tau, or cTau7 and cTau 12 from the assay.

Results

CSF Cleaved Tau Monoclonal Antibodies

CSF from CNS injury and control patients was immunoblotted with Mab Tau-1 whose epitope has been mapped to $ser^{199}$ of tau. Distinct but modest Tau-1 labeling of CSF proteins in the 30 kDa to 50 kDa region was observed in CNS injury patients while no immunoreactivity occurred in control patients (FIG. 1). MAbs recognizing these 30 kDa to 50 kDa CSF cleaved tau proteins were developed by subjecting hybridoma supernatants to a differential solid phase ELISA screen employing CSF samples from CNS injury and control patients. Three monoclonal producing hybridomas, cTau7, cTau8 and cTau12 were selected that maximally discriminated between CNS injury and control CSF (FIG. 1). For example, cTau7 CSF inumunoblot data from four CNS trauma patients are shown in FIG. 1. CSF samples in the first and third lanes were from two different closed head injury patients with intracranial hemorrhage while CSF samples in the second and fourth lanes were from two different patients with subarachnoid hemorrhage secondary to rupture of the anterior communicating artery. All patients were admitted with a Glasgow Coma Score less than 7 and demonstrated elevated intracranial pressure requiring placement of an intraventricular shunt. All four CNS trauma patients demonstrated significant cTau7 labeled CSF proteins in the 30 kDa to 50 kDa range. In comparison, control patients demonstrated no cTau7 immunoreactivity (FIG. 1). Similar results were observed with CSF samples immunoblotted with cTau10 and cTau12 (data not shown). The developed MAbs resulted in more intense labeling of CNS trauma patient CSF than Tau-1. Split CSF samples with equivalent protein loads were blotted with Tau-1 (FIG. 1, left panel, lanes a and b) and cTau7 (FIG. 1, right panel, CNS trauma, lanes a and b) with cTau7 producing more intense labeling.

Characterization of cTau7, cTau8 and cTau12 Labeled Proteins

The following materials relevant to the experiments described have been deposited with the American Type Culture Collection, in Manassas, Va., on Feb. 8, 2002:

| Identification Reference by Depositor | Pat. Deposit Designation |
| --- | --- |
| Mouse Lymphocytes: C-tau 7 | PTA-4061 |
| Mouse Lymphocytes: C-tau 8 | PTA-4062 |
| Mouse Lymphocytes: C-tau 12 | PTA-4063 |

The experiments described below indicate that the 30 kDa to 50 kDa proteins recognized by antibodies cTau7, cTau8 and cTau12 are a cleaved form of the microtubule binding protein tau. These data demonstrate that: 1) antibodies cTau7, cTau8 and cTau12 label recombinantly expressed tau, 2) that the 30 kDa to 50 kDa proteins recognized by cTau7, cTau8 and cTau12, similar to tau, contain a functionally intact microtubule binding domain, 3) antibodies cTau7, cTau8 and cTau12 label a 14.7 kDa CNBr digestion fragment comprised of pro$^{215}$ to met$^{419}$ of the tau primary sequence, 4) 30 kDa to 50 kDa cleaved tau proteins occur in both CSF from CNS trauma patients and post mortem brain and 5) epitope mapping studies suggest that CSF 30 kD to 50 kD proteins consist of the interior portion of the tau sequence from which the N- and C-terminal amino acids have been cleaved.

Recombiniant Tau Immunoreactivity.

Figure 2:
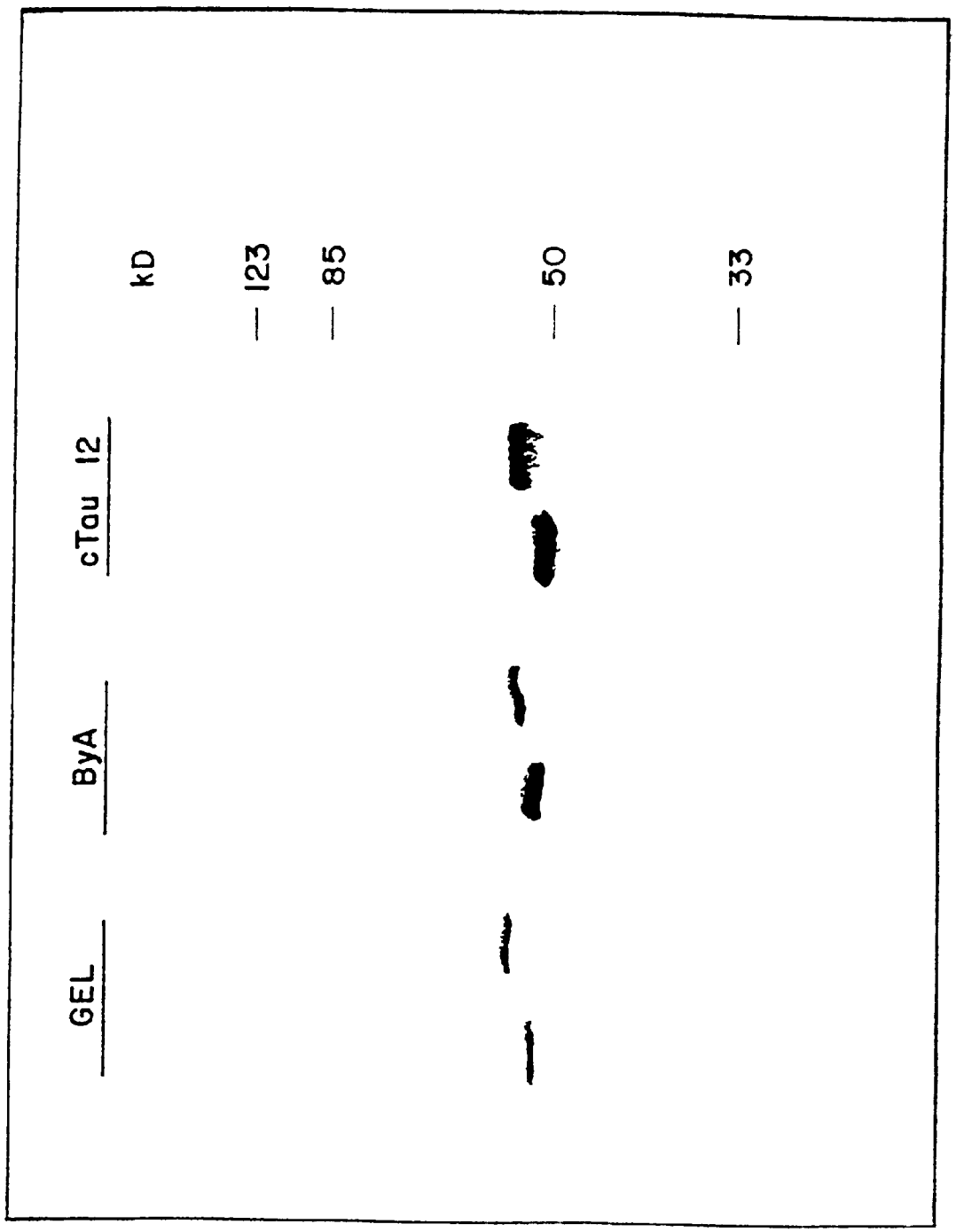
FIG. 2. CSF cleaved tau MAbs label recombinant tau. Commassie Blue stained 10% gel with recombinant 3-repeat tau (Gel, left lane, 1 µg) and 4-repeat tau (Gel, right lane, 1 µg). Recombinant tau blotted with BYA (0.07 µg/lane) and cTau12 (2.5 µg/lane). Molecular weight markers shown at right.

MAbs cTau7, cTau8 and cTau12 labeled recombinant tau expressed in E. coli (FIG. 2). Recombinant tau containing either three repeats or four repeats was expressed in BL21 (DE3) cells and isolated. Recombinant tau was highly purified as judged by Commassie Blue stained SDS-PAGE (FIG. 2, Gel). Both tau isoforms demonstrated immunoreactivity with tau polyclonal antibody BYA and at higher protein loads MAbs cTau 12 (FIG. 2), cTau7 and cTau8 (data not shown).

Figure 3:
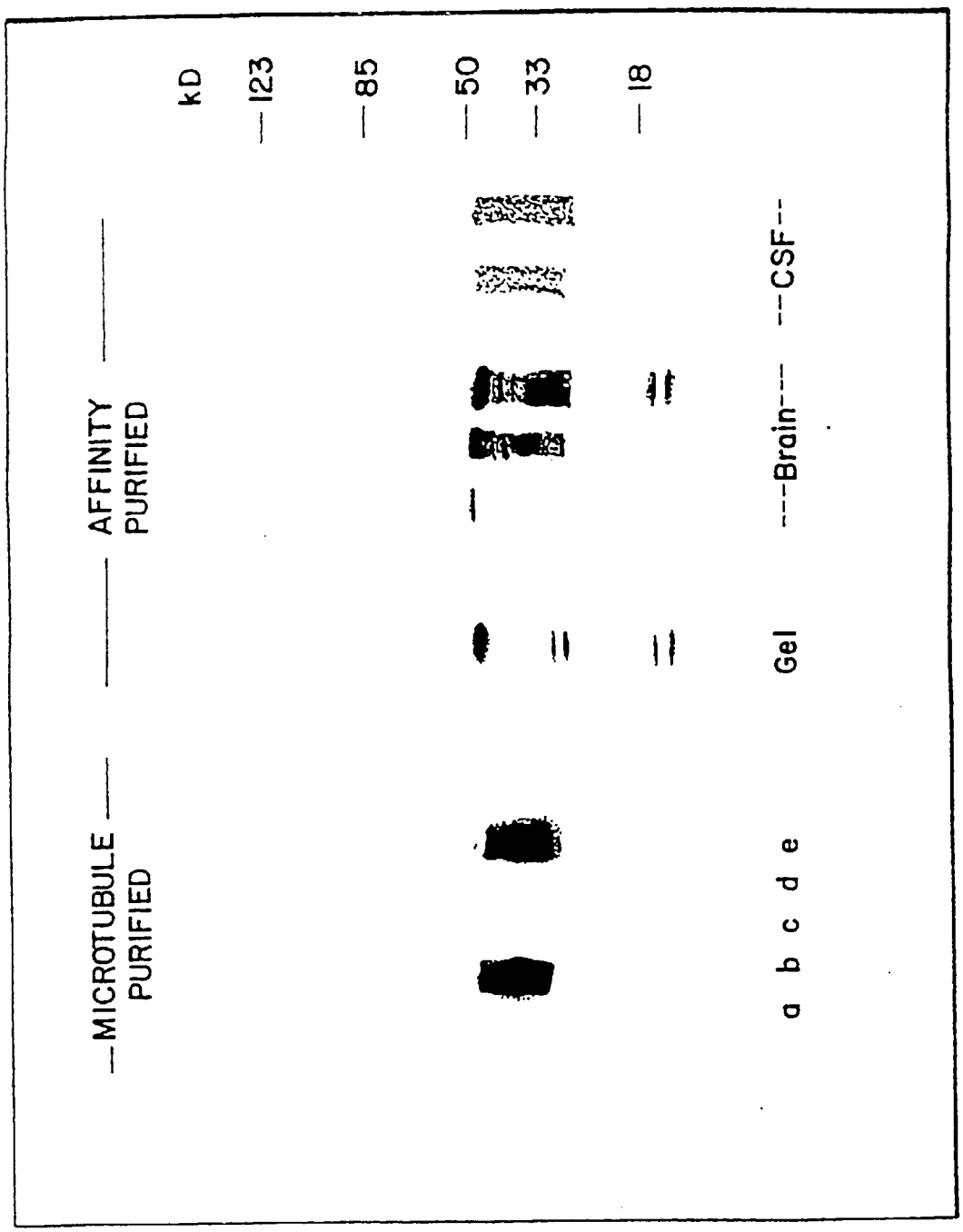
FIG. 3. CSF cleaved tau proteins bind microtubules. Microtubule Purified: Initially, taxol polymerized microtubules were salt extracted to insure that no cTau7 immunoreactive proteins were present (lane a). Microtubules were then incubated with a preparation of CSF cleaved tau proteins (lane b, 1 μg) and washed several times until the supernatant was free of cTau7 reactivity (lanes c and d). Microtubule bound proteins were salt extracted yielding 30 kD to 50 kD cTau7-reactive cleaved tau proteins (lane e). Similar results were obtained with MAbs cTau8 and cTau12 (data not shown). Affinity Purified: CSF cleaved tau proteins were affinity-purified with MAbs cTau7, cTau8 and cTau12 coupled to Protein G agarose. Commassie Blue stained gels indicated that affinity purified cleaved tau consisted of a primary 50 kD protein band (gel, 1 μg). Immunoblots with cTau7 revealed a single protein band when 10 nanograms (ng) of affinity purified cleaved tau protein was loaded; lower molecular weight cTau7 reactive proteins were detected with larger protein loads (30 and 100 ng). Similar results were observed with MAbs cTau8 and cTau12 (data not shown).

Affinity and microtubule purification of tau. CSF from CNS trauma patients or a preparation of heat-stable brain proteins was affinity purified with MAbs cTau7, -8 and -12 (FIG. 3). Affinity purification from either source revealed a band of 30 kDa to 50 kDa tau proteins on immunoblotting or on Commassie Blue stained SDS-PAGE (FIG. 3, Affinity Purified). These data suggest that 30 kDa to 50 kDa tau proteins are cleaved in brain and then gain access to CSF.

Figure 5:
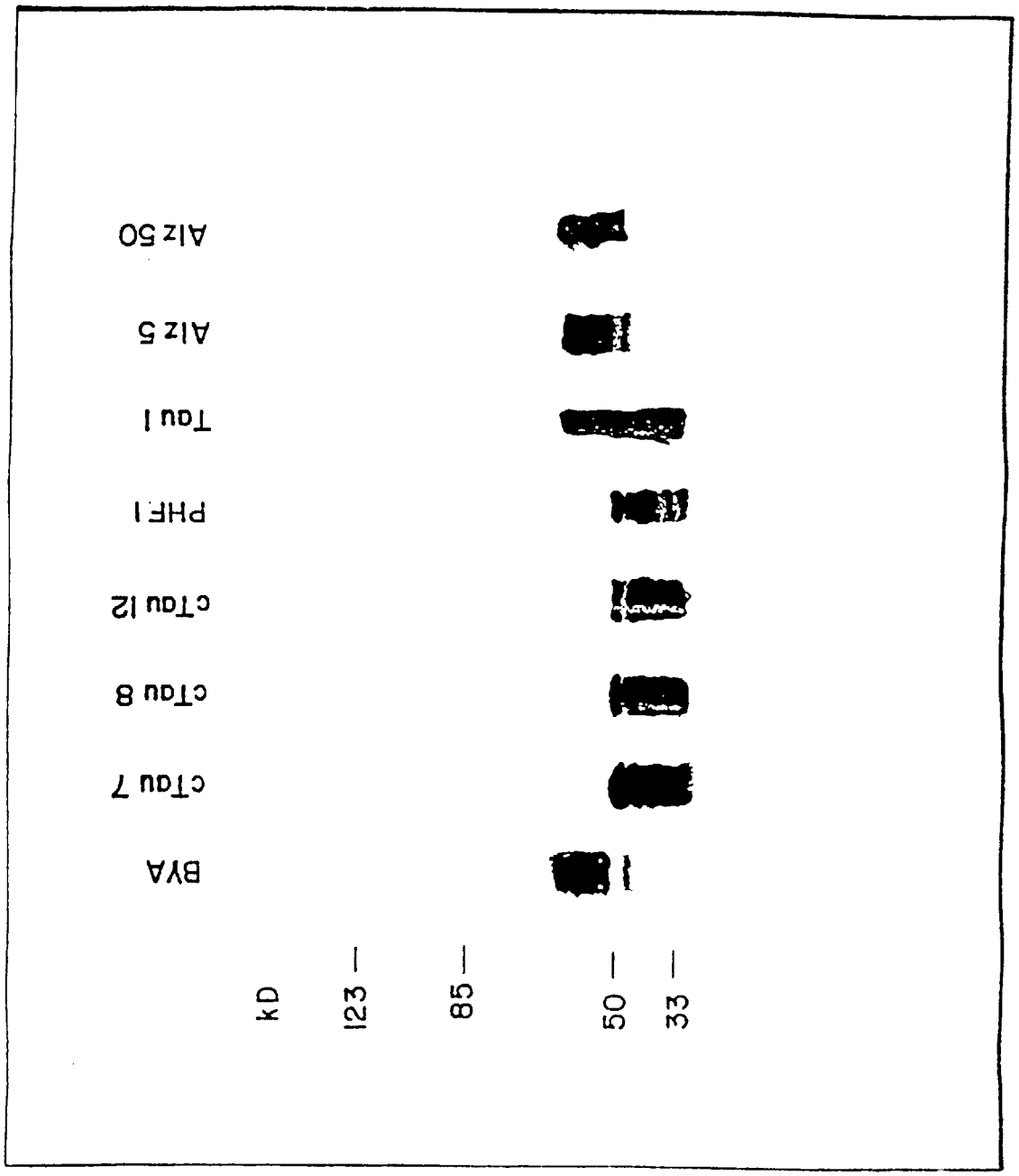
FIG. 5. CNS trauma brain contains both full length 48 kD to 68 kD tau proteins and 30 kD to 50 kD cleaved tau proteins. Full length brain tau proteins were selectively labeled with the tau antibody BYA, the C-terminal tau antibody Alz5 and the N-terminal tau antibody Alz50. Cleaved tau proteins were selectively labeled with MAbs cTau7, cTau8, cTau12 and PHF1 that recognizes phospho-ser$^{396}$ of tau. Mab Tau-1 that recognizes non-phosphorylated ser$^{199}$ of tau labeled both forms of tau. These data suggest that tau is cleaved and phosphorylated at ser$^{199}$ in brain.

Similar to tau, CSF and brain 30 kDa to 50 kDa proteins recognized by MAbs cTau7, cTau8 and cTau12 bind microtubules. Tubulin was purified from brain and polymerized into mictotubules with taxol. Endogenous microtubule binding proteins were dissociated from the polymerized microtubules with all detectable endogenous MAPs removed by the third salt extraction (FIG. 3, lane a). Microtubules were incubated with CSF 30 kDa to 50 kDa cleaved-tau proteins (FIG. 3, lane b) and microtubules washed several times to remove all proteins not tightly bound (FIG. 3, lanes c and d). Microtubule binding proteins were then salt extracted from the washed microtubule preparation revealing a cTau7-labeled ladder of 30 kDa to 50 kDa proteins (FIG. 5, lane e). Similar results were obtained with MAbs cTau8 and cTau12 (data not shown). No labeling of MAP2 or neurofilaments with MAbs cTau7, 8 and 9 was observed in the microtubule purified brain preparation. The presence of 280 kDa MAP2 in this preparation was confirmed by immunoblots with Mab AP-14 (Kalcheva et al., 1994) which labels both MAP2a and MAP2b while the presence of 200 kDa neurofilament-H and 155 kDa neurofilament-M was confirmed with MAbs NE-14 (Gotow and Tanaka, 1994) and BF-10 (Anderton et al., 1982), respectively (data not show).

Figure 4:
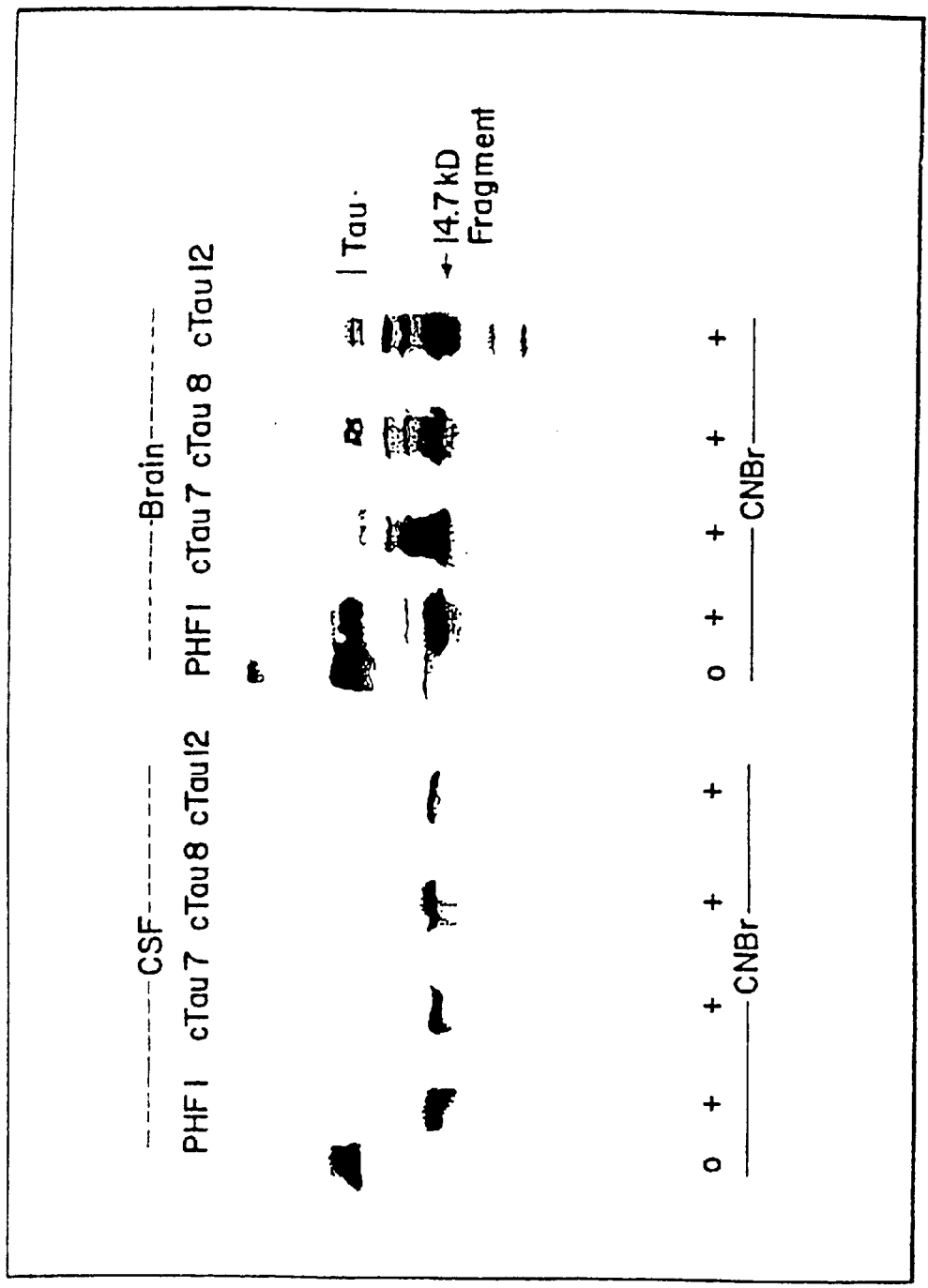
FIG. 4. MAbs cTau7, cTau8 and cTau12 recognize a 14.7 kDa CNBr cleaved tau digestion fragment occurring in patient CSF or Brain. Cleaved tau from CSF or brain (2 μg/lane) was treated either with (+) or without (0) CNBr and blotted with MAbs PHF-1, cTau7, cTau8 and cTau12. All four antibodies predominantly labeled the same CNBr digestion fragment in both CSF and brain consisting of pro$^{251}$ to met$^{419}$ of tau. The PHF-1 fragment has a reported molecular weight of 14.7 kDa (Zemlan and Dean, 1996). Blots are from a 15% gel. The position at which non-digested cleaved tau migrated is shown (Tau).

Epitope mapping. cTau7, -8 and -12 immunoblots of CNBr digested CSF or brain 30 kDa to 50 kDa tau proteins indicated that all three MAbs labeled the same CNBr fragment (FIG. 4). This fragment could also be labeled with the Mab PHF-1 which recognizes phosphorylated ser$^{396}$ of tau (Otvos et al, 1994; Zemlan et al., 1996). The PHF- 1 data identify the cTau7, cTau8 and cTau12 labeled fragment as the largest CNBr digestion product that is comprised of tau sequences pro to met. These data indicate that both CSF and brain cleaved tau proteins demonstrate similar CNBr digestion products suggesting that the labeled CSF and brain proteins are structurally similar.

Tau antibody BYA raised against full length tau labeled a band of 48 kDa to 68 kDa proteins in heat-stable extracts of post mortem brain (FIG. 5). In comparison, antibodies cTau7, -8 and -12 labeled a band of 30 kDa to 50 kDa proteins indicating that these cTau MAbs labeled proteins demonstrating an greater gel mobility than intact tau. Further, these data indicate that MAbs cTau7, cTau8 and cTau12 have limited affinity for intact, full length tau. Mab PHF-1 also selectively labeled a band of 30 kDa to 50 kDa proteins indicating that these proteins differ from intact tau both by cleavage and phosphorylation at ser$^{396}$ (FIG. 5, PHF1). Mab Tau-1 labeled proteins spanning the 30 kDa to 68 kDa region indicating that ser$^{199}$ is poorly phosphorylated in both full length and cleaved tau (FIG. 5, Tau1). In comparison, the C-terminal antibody Alz5 and the N-terminal antibody Alz50 labeled only full length tau suggesting that these epitopes are not present in cleaved tau.

To determine whether tau cleavage occurred in CSF, 5 µg of recombinant tau was added to 1 ml of CSF and incubated overnight at 37° C. CSF aliquots were run on SDS-PAGE and blotted with BYA which indicted the presence of intact, non-cleaved tau in all cases.

Prior to sandwich ELISA development, it was important to determine whether cTau7, cTau 8 and cTau 12 epitopes were independent and whether the epitopes were phosphorylated. ELISA competition studies between cTau7, cTau 8 and cTau12 resulted in non-competitive binding to CSF tau proteins (data not shown). Also, MAbs cTau7, cTau 8 and cTau 12 demonstrated phosphorylation independent binding to 30 kDa to 50 kDa cleaved tau proteins. For example, BAP treatment produced a 5 fold increase in the binding of Mab SM133 which recognizes non-phosphorylated ser$^{235}$ of tau (BAP: 1.88, no BAP: 0.35, mean O.D.) while no effect of BAP treatment on cTau7 (BAP: 1.75, no BAP 1.51), cTau8 (BAP: 1.99, no BAP: 1.61) or cTau12 (BAP: 1.72, no BAP: 1.53) binding was observed.

Cleaved Tau Sandwich ELISA and Axonal Degeneration

Figure 6:
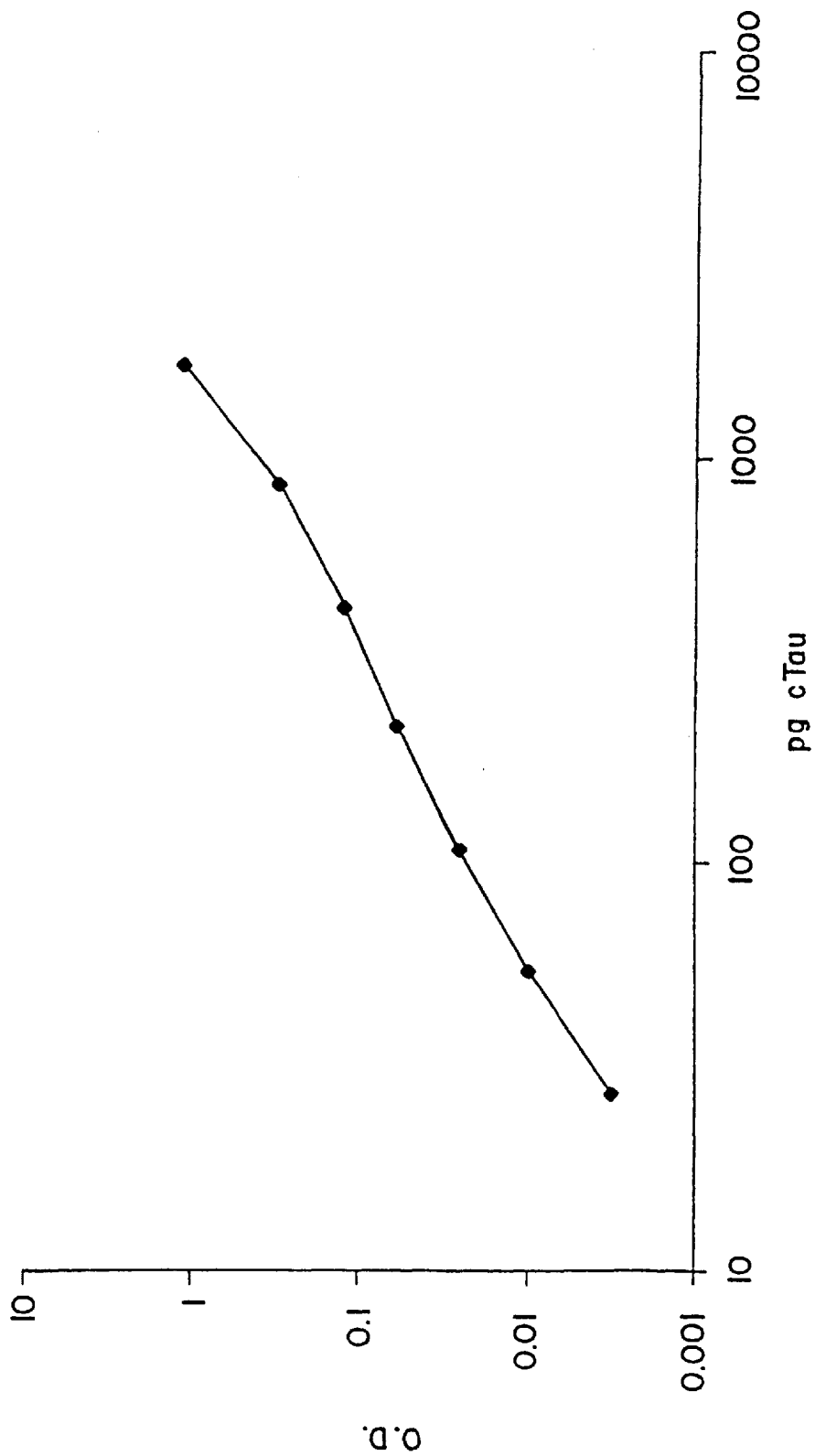
FIG. 6. Titration of affinity purified CSF cleaved tau employing the developed cleaved tau ELISA. A catalyzed-reporter deposition sandwich ELISA was developed employing cTau12 as capture antibody and HRP-conjugated cTau7 and cTau8 for detection. Affinity purified CSF cleaved tau was used as standard. All concentrations (pg/well) were tested in triplicate and values represent the mean O.D. value.

A sensitive ELISA using catalyzed reporter deposition for signal enhancement was developed using Mab cTau12 for antigen capture, HRP-conjugated MAbs cTau7 and cTau8 for detection, and biotin-tyramine as the reporter. The sensitivity of this ELISA for affinity purified CSF tau was about 0.030 ng to 0.040 ng per well (FIG. 6).

This ELISA was employed to measure CSF cleaved tau levels in patients undergoing active axonal degeneration. CSF was obtained from 131 patients. Samples were collected from patients with axonal degeneration resulting from acute CNS injury and three control groups free of axonal degeneration (demyelinating disease, neurologic controls and normal controls). The CNS injury group consisted of patients with acute severe brain injury resulting from trauma or intracranial aneurysmal rupture. The demyelinating disease group consisted exclusively of patients with multiple sclerosis (N=41). The neurologic control group consisted of patients with migraine or vascular headache (N=9), dementia not associated with a neurodegenerative disease (N=11), myotonic disorder (N=4), seizure disorder (N=3), Guillian-Barre syndrome (N=2), hydrocephalus (N=2), seizure disorder (N=2), transverse myelitis (N=2) or other neurologic disorder (N=3). The normal control group were individuals with no known neurologic disease. They consisted of family members of patients with a neurologic disease (N=10), patients with a psychiatric disorder (N=13) or patients hospitalized for a non-neurologic disorder (N=18).

CSF cleaved tau levels were significantly elevated in patients with axonal degeneration following CNS injury (Table 1). CSF cleaved tau levels were elevated over 10,000 fold in CNS injury patients when compared to patients without axonal degeneration, i.e. a demyelinating disease ($p<0.001$), or neurologic controls ($p<0.001$) or normal controls ($p<0.001$). Further, no overlap between CNS injury CSF cleaved tau levels and patients in any control group were observed. Only two of the 41 patients in the demyelinating disease group demonstrated detectable tau levels and both values were significantly lower than those observed in the CNS injury group. Similarly, CSF cleaved tau levels were not detectable in most control patients. Among neurologic controls only two of 38 patients had detectable CSF tau levels. These were patients with Guillian Barre syndrome (0.464 ng/ml) or cerebral ischemia (0.433 ng/ml). Only one of 41 normal control patients demonstrated detectable tau levels. This was a cardiac transplant patient (0.927 ng/ml).

Serum cleaved-tau levels were significantly elevated in patients with acute CNS trauma (moderate to severe traumatic brain injury) compared to control patients (Table 2). In patients with traumatic brain injury, serum cleaved-tau levels varied from a low of 0.14 ng/ml serum to a high of 4.56 ng/ml serum. Serum cleaved-tau levels in non-neurologic control patients were over 40 fold lower than levels observed in brain injured patient. Only one non-neurologic control patient (1/19) demonstrated a serum cleaved-tau level that fell within the range of patients with traumatic brain injury. All neurologic control patients (N=22) demonstrated non-detectable levels of serum cleaved-tau and therefore demonstrated no overlap with the patients with traumatic brain injury.

Conclusion

In the present disclosure, a novel cleaved form of tau is described in CSF and blood. This truncated form of tau was reactive with the three MAbs developed in the present study and tau antibodies raised in other laboratories (FIGS. 1 and 5). The present data indicate that only cleaved tau and not full length 48 kDa to 68 kDa tau proteins are present in CSF (Cleveland et al., 1977; Couchie and Nunez, 1985). Consistent with these data, differential CSF hybridoma screening identified three MAbs that demonstrated high affinity for the cleaved form of tau found in CSF but limited affinity for intact, full length tau (FIG. 5). For example, MAbs cTau7, cTau8 and cTau12 demonstrated selective labeling of cleaved tau when equivalent protein loads of cleaved tau and intact were examined by Western blot (FIG. 5). Similarly, thirty fold greater protein loads of full length recombinant tau were required to demonstrate labeling with cTau7, cTau8 and cTau12 than with antibodies raised against full length tau (FIG. 2).

The selectivity of MAbs cTau7, cTau8 and cTau12 for cleaved tau is best explained by a conformational state assumed by tau following cleavage rather than differences in primary sequence or phosphorylation. Previous research demonstrates that MAbs can specifically recognize tau secondary structure. Several tau MAbs including Alz50, Tau-2 and MC1 recognize a specific tau conformation rather than tau primary structure (Carmel et al., 1996; Vincent et al., 1996). For example, using tau deletion mutants Carmel et al. (1996) demonstrated that Alz50 recognized a conformation of tau where the N-terminus is in close association with the microtubule binding domain. The $K_d$ of Alz50 for the native tau protein in this preferred conformation was over 70 fold higher than for the protein without the preferred secondary structure. Similarly, MAbs cTau7, cTau8 and cTau12 appear to recognize a secondary structure that tau assumes after cleavage. The present CNBr, epitope mapping and microtubule binding data indicate that 30 kDa to 50 kDa CSF cleaved tau proteins are comprised of the interior portion of the tau primary sequence including a functionally intact microtubule binding domain (FIGS. 3, 4 and 5).

The present data indicate that CSF levels of cleaved-tau reflect the extent of CNS axonal degeneration. CSF cleaved-tau levels were elevated 10,000 fold over control levels in patients hospitalized for CNS injury. Further, there was no overlap of CSF cleaved tau levels between acute CNS injury patients and controls. The sequelae of CNS injury is characterized by extended parenchymal atrophy and axonal degeneration (Adams et al., 1989). Microtubule-associated protein tau is a neuron-specific cytoskeletal protein localized in the axonal compartment. The present data indicate that axonal degeneration is associated with significant release of cleaved tau into CSF.

TABLE 1

CSF cleaved tau levels and demographic data for patients with CNS injury and three control groups (demyelinating disease, neurologic and normal controls).

| | CSF cleaved-Tau (ng/ml) | | | Age | | |
|---|---|---|---|---|---|---|
| Diseases | mean | range | SD | mean | SD | N |
| CNS Injury[a,b,c] | 396.96 | 2.5–2,361 | 741.58 | 47.4 | 15.2 | 11 |
| Demyelinating | 0.005 | 0–0.21 | 0.03 | 40.3 | 10.3 | 41 |
| Neurologic Controls | 0.024 | 0–0.50 | 0.10 | 52.2 | 17.5 | 38 |
| Normal Controls | 0.023 | 0–0.93 | 0.15 | 53.8 | 16.0 | 41 |

Analysis of variance of CSF tau levels for four patients groups, $p < 0.001$.
[a] CSF tau levels are significantly different from neurologic control group, $p < 0.001$.
[b] CSF tau levels are significantly different from normal control group, $p < 0.001$.
[c] CSF tau levels significantly elevated from demyelinating disease group, $p < 0.001$.

TABLE 2

Serum cleaved-tau levels for moderate to severe traumatic brain injury patients and neurologic and non-neurologic controls **Significantly different from other groups $p < 0.001$.

| | Serum cleaved-tau (ng/ml) | | |
|---|---|---|---|
| Diseases | Mean | range | N |
| CNS Injury | 1.457** | 0.14–4.56 | 11 |
| Neurologic Controls | 0.000 | 0–0 | 22 |
| Non-neurologic Controls | 0.034 | 0.000–0.650 | 19 |

References

Adams J. H., Doyle D., Ford I., Gennarelli T. A., Graham D. I., and McLellan D. R. (1989) Diffuse axonal injury in head injury: definition, diagnosis and grading. *Histopathology* 15, 49–59.

Anderton B. H., Breinberg D., Downes M. J., Green P. J., Tomlinson B. E., Ulrich J., Wood J. N., and Kahn J. (1982) Monoclonal antibodies show that neurofibrillary tangles and neurofilaments share antigenic determinants. *Nature* 298, 84–86.

Binder L. I., Frankfurter A., and Rebhun L. I. (1985) The distribution of tau in the mammalian central nervous system. *J. Cell Biol.* 101, 1371–1378.

Bobrow M. N., Harris T. D., Shaughnessy K. J. and Litt G. J. (1989) Catalyzed reporter deposition, a novel method of signal amplification. *J. Immunol. Meth.* 125, 279–285.

Boorsma D. M. and Kalsbeek G. L. (1975) A comparative study of horseradish peroxidase conjugates prepared with a one-step and a two-step process. *J. Histochem. Cytochem.* 23, 200–207.

Caputo C. B., Wischik C., Novak M., Scott C. W., Brunner W. F., De Garcini E. M., Lo M. M. S., Norris T. E. and Salama A. I. (1992) Immunological characterization of the region of tau protein that is bound to Alzheimer paired helical filaments. *Neurobiol. Aging* 13, 267–274.

Carmel G., Mager E. M., Binder L. I. and Kuret J. (1996) The structural basis of monoclonal antibody Alz50's selectivity for Alzheimer's disease pathology. *J. Biol. Chem.* 271, 32789–32795.

Chan S.-O. and Chiu F.-C. (1995) Cloning and developmental expression of human 66 kd neurofilament protein. *Mol. Brain Res.* 29, 177–184.

Cleveland D. W., Hwo S. Y. and Kirschner M. W. (1977) Purification of tau, a microtubule-associated protein that induces the assembly of microtubules from purified tubulin. *J. Mol. Biol.* 116, 207–225.

Couchie D. and Nunez J. (1985) Immunological characterization of microtubule-associated proteins specific for the immature brain. *FEBS Lett.* 188, 331–335.

Goedert M., Spillantini M. G., Jakes R., Rutherford D. and Crowther R. A. (1989) Multiple isoforms of human microtubule-associated protein tau: sequence and localization in neurofibrillary tangles and Alzheimer's disease. *Neuron* 3, 519–526.

Gotow T. and Tanaka J. (1994) Phosphorylation of neurofilament H subunit as related to arrangement of neurofilaments. *J. Neurosci. Res.* 37, 691–713.

Greenberg S. G., Davies P., Schein J. D. and Binder L. I. (1992) Hydrofluoric acid-treated PHFτ proteins display the same biochemical properties as normal τ. *J. Biol. Chem.* 267: 564–569.

Hayes R. L., Yang K., Whitson J. S. and Posmantur R. (1995) Cytoskeletal deragements following central nervous system injury: modulation by neurotropic gene transfection. *J. Neurotrauma* 12, 933–941.

Julien J. P., Grosveld F., Yazdanbaksh K. et al.: The structure of the hunan neurofilament gene (NF-L): a unique exon-intron organization in the intermediate gene family. *Biochim. Biophys. Acta* 909, 10–20.

Kohler G. and Milstein C. (1975) Continuous cultures of fused cells secreting antibody of predefined specificity. *Nature* 256, 495–497.

Kosik K. S. and Finch E. A. (1987) MAP2 and tau segregate into dendritic and axonal domains after the elaboration of morphologically distinct neurties. *J. Neurosci.* 7, 3142–3153.

Kosik K. S., Orecchio L. D., Bakalis S. and Neve R. L. (1989) Developmentally regulated expression of specific tau sequences. *Neuron* 2, 1389–1397.

Laemmli, U. K. (1970) Cleavage of structural proteins during the assembly of the head of bacteriophage T4. *Nature* 227, 680–685.

Lee G. and Rook S. L. (1992) Expression of tau protein in non-neuronal cells: microtubule binding and stabilization. *J. Cell Sci.* 102, 227–237.

Lees J. F., Shneidman P. S., Skuntz S. F. et al.: The structure and organization of the human heavy neurofilament subunit (NF-H) and the gene encoding it. *EMBO J.* 7, 1947–1955.

Litman P., Barg J., Rindzoonski L. and Ginsburg I. (1993) Subcellular localization of tau mRNA in differentiating neuronal culture: implications for neuronal polarity. *Neuron* 10, 627–638.

Myers M. W., Lazzarini R. A., Lee V. M. et al.: (1987) The human mid-size neurofilament subunit: a repeat protein sequence and the relationship of its gene to the intermediate filament gene family. *EMBO J.* 6, 1617–1626.

Nukina N., Kosik K. S. and Selkoe D. J. (1987) Recognition of Alzheimer's paired helical filaments by monoclonal neurofilament antibodies is due to crossreaction with tau protein. *Proc. Natl. Acad. Sci. USA* 84, 3415–3419.

Otvos L., Feiner L., Lang E., Szendrei G. I., Goedert M. and Lee V. M. Y. (1994) Monoclonal antibody PHF-1 recognizes tau protein phosphorylated at serine residues 396 and 404 *J. Netirosci. Res.* 39, 669–673.

Schiff P. B., Fant J. and Horwitz S. B. (1979) Promotion of microtubule assembly in vitro by taxol. *Nature* 277, 665–667.

Shaw G. (1986) Neurofilaments: abundant but mysterious structures. *Bioessays* 4, 161–166.

Towbin H., Staehelin T., and Gordon J. (1979) Electrophoretic transfer of proteins from polyacrylamide gels to nitrocellulose sheets: Procedure and some applications. *Proc. Natl. Acad. Sci USA* 76, 4350–4354.

Vallee R. B. (1982) A taxol-dependent procedure for the isolation of microtubules and microtubule-associated proteins (MAPs). *J. Cell Biol.* 92, 435–442.

Vincent I., Rosado M. and Davies P. (1996) Mitotic mechanisms in Alzheimer's disease?. *J. Cell Biol.* 132, 413–425.

Wolozin B. L., Pruchnicki A., Dickson D. W., and Davies P. (1986) A novel antigen in the Alzheimer's brain. *Science* 232, 648–650.

Zemlan F. P. and Dean G. E. (1996) Monoclonal antibody PHF-9 recognizes phosphorylated ser404 of tau protein and labels paired helical filaments. *J. Neurosci. Res.* 46, 90–97.

I claim:

1. A method for detecting and quantitating axonally-derived tau protein in a human subject, comprising:

(a) contacting a blood sample from a human subject with an antibody capable of binding to the tau protein;

(b) detecting the bound tau protein; and (c) determining the amount of bound tau protein based upon detection of the bound protein.

2. The method of claim 1 wherein the antibody is selected from the group consisting of an antibody substantially free of natural impurities, a monoclonal antibody; and mixtures, fragments or derivatives thereof, wherein said fragments or derivatives bind tau protein.

3. The method of claim 2 comprising the additional step of comparing the amount of bound axonally-derived tau protein to control samples selected from the group representing a normal undamaged axon state and those representing an axonal damage state.

4. The method according to claim 3 wherein the binding molecule is detectably labeled.

5. The method according to claim 4 wherein the detection indicates that the subject has traumatic central nervous system injury.

6. The method according to claim 5 wherein the protein is a fragment of tau protein demonstrating an apparent molecular weight less than 50 kDa, as measured by SDS-PAGE under denaturing conditions.

7. The method according to claim 6 wherein the fragment demonstrates an apparent molecular weight in the range of about 30 kDa to about 50 kDa, as measured by SDS-PAGE under denaturing conditions.

8. The method according to claim 6 wherein the fragment comprises the native amino acid sequence from serine$^{199}$ to serine$^{396}$ of the tau protein.

9. The method according to claim 8 wherein the fragment lacks the native N-terminal and C-terminal amino acids.

10. The method of claim 1 comprising the measurement of bound tau proteins using an ELISA technique.

11. The method of claim 10 wherein the monoclonal antibodies comprise MAbs cTau7, cTau8 and/or cTau12.

12. The method of claim 10 wherein said ELISA is a tau sandwich ELISA.

13. A method according to claim 1 wherein the bound axonally-derived protein is a fragment of tau protein which is detected through gel electrophoresis which indicates multiple protein bands with apparent molecular weights less than 50 kDa.

14. A method according to claim 1 wherein the bound axonally-derived protein is a fragment of tau protein which is detected through gel electrophoresis which indicates multiple protein bands with apparent molecular weights from about 30 to about 50 kDa, as measured by SDS-PAGE under denaturing conditions.

15. A method for detecting traumatic central nervous system (CNS) injury by the quantification of total tau protein comprising:
(a) contacting a sample from a patient suspected of traumatic central nervous system injury with a monoclonal antibody produced by hybridoma cTau7, hybridoma cTau8 or hybridoma cTau12, alone or in combination under conditions that form a tau-antibody complex, wherein said sample is a blood sample or a sample isolated from blood;
(b) quantifying the amount of total tau protein by detecting the amount of total tau protein in a tau-antibody complex, wherein an increase in the amount of total tau protein when compared to a normal healthy control is indicative of disease.

16. The method for the quantification of total tau protein comprising:
(a) contacting a sample from a patient suspected of traumatic CNS injury with a monoclonal antibody produced by hybridoma cTau7, hybridoma cTau8 or hybridoma cTau12, alone or in combination under conditions that form a tau-antibody complex, wherein said sample is a blood sample or a sample isolated from blood;
(b) quantifying the amount of total tau protein in said patient blood sample or sample isolated from blood by detecting the amount of total tau protein in a tau-antibody complex and comparing said patient blood sample to the amount of total tau protein in a tau-antibody complex of a sample isolated from human brain.

* * * * *

UNITED STATES PATENT AND TRADEMARK OFFICE
CERTIFICATE OF CORRECTION

PATENT NO. : 6,589,746 B1 Page 1 of 1
DATED : July 8, 2003
INVENTOR(S) : Zemlan, F.

It is certified that error appears in the above-identified patent and that said Letters Patent is hereby corrected as shown below:

Column 25,
Line 9, add, -- ..., as measured by SDS-PAGE under denaturing conditions. --.

Signed and Sealed this

Twenty-fifth Day of April, 2006

JON W. DUDAS
*Director of the United States Patent and Trademark Office*